United States Patent [19]

Suchy et al.

[11] Patent Number: 5,183,492
[45] Date of Patent: Feb. 2, 1993

[54] HERBICIDAL 3-ARYLURACILS

[75] Inventors: Milos Suchy, Pfaffhausen; Paul Winternitz, Greifensee; Martin Zeller, Baden, all of Switzerland

[73] Assignee: Ciba-Geigy Corporation, Ardsley, N.Y.

[21] Appl. No.: 656,133

[22] Filed: Feb. 27, 1991

[30] Foreign Application Priority Data

Jun. 29, 1989 [CH] Switzerland .......................... 2450/89

[51] Int. Cl.⁵ ................... A01N 43/54; C07D 239/54; C07D 239/70; C07D 239/96
[52] U.S. Cl. .................................... 504/243; 544/309; 544/311; 544/312; 544/313; 544/314; 504/240; 504/193; 504/197
[58] Field of Search ............... 544/309, 311, 312, 313, 544/314, 243, 229; 71/92

[56] References Cited

U.S. PATENT DOCUMENTS

| | | | |
|---|---|---|---|
| 3,235,360 | 2/1966 | Soboczenski | 71/2.5 |
| 3,235,363 | 12/1966 | Luckenbaugh et al. | 71/2.5 |
| 3,291,592 | 12/1966 | Evans | 71/2.5 |
| 3,360,520 | 12/1967 | Luckenbaugh et al. | 260/260 |
| 4,746,352 | 5/1988 | Wenger et al. | 544/314 |
| 4,760,163 | 7/1988 | Wenger et al. | 544/314 |
| 4,812,164 | 3/1989 | Wenger et al. | 71/92 |
| 4,859,229 | 8/1989 | Wenger et al. | 544/314 |
| 4,927,451 | 5/1990 | Brouwer et al. | 544/314 |
| 4,941,909 | 7/1990 | Wenger et al. | 544/314 |
| 5,084,084 | 1/1992 | Satow et al. | 544/314 |

FOREIGN PATENT DOCUMENTS

| | | |
|---|---|---|
| 195346 | 9/1986 | European Pat. Off. |
| 255047 | 2/1988 | European Pat. Off. |
| 260621 | 3/1988 | European Pat. Off. |
| 1924232 | 5/1969 | Fed. Rep. of Germany |
| 482402 | 1/1970 | Switzerland |
| 968661 | 9/1964 | United Kingdom |
| 968666 | 9/1964 | United Kingdom |
| 1035096 | 7/1966 | United Kingdom |
| 1035097 | 7/1966 | United Kingdom |
| 1035098 | 7/1966 | United Kingdom |

Primary Examiner—Cecilia Tsang
Attorney, Agent, or Firm—Wenderoth, Lind & Ponack

[57] ABSTRACT

The invention is concerned with compounds of the formula

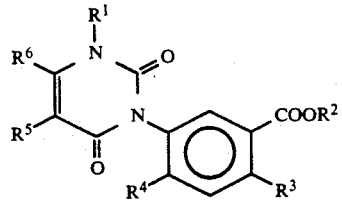

wherein $R^1$, $R^2$, $R^3$, $R^4$, $R^5$ and $R^6$ have the significances given in the description, as well as enol ethers and salts thereof and their manufacture. The compounds have herbicidal properties and are accordingly suitable as active ingredients of weed control compositions. The invention is also concerned with weed control compositions containing one or more of such substances and with the use of the substances or compositions for the control of weeds.

15 Claims, No Drawings

HERBICIDAL 3-ARYLURACILS

The present invention is concerned with heterocyclic compounds, namely 3-aryluracils of the general formula

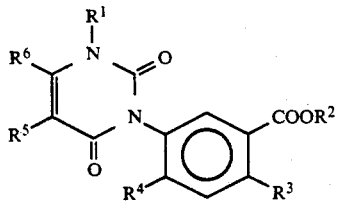
I wherein
$R^1$ signifies hydrogen, $C_{1-4}$-alkyl, $C_{3 \text{ or } 4}$-alkenyl, $C_{3 \text{ or } 4}$-alkynyl or $C_{1-4}$-haloalkyl,
$R^2$ signifies $C_{1-6}$-alkylsulphonyl-$C_{1-4}$-alkyl, di($C_{1-6}$-alkyl)phosphono-$C_{1-4}$-alkyl, tri($C_{1-6}$-alkyl)silyl-$C_{1-4}$-alkyl, $C_{2-7}$-alkanoyl-$C_{1-4}$-alkyl, carboxy-$C_{1-4}$-alkyl, ($C_{1-6}$-alkoxy)carbonyl-$C_{1-4}$-alkyl, {[$C_{3-9}$-(60-alkylalkylidene)]iminooxy-($C_{1-6}$-alkoxy)carbonyl}-$C_{1-4}$-alkyl, ($C_{3-6}$-alkenyloxy)carbonyl-$C_{1-4}$-alkyl, ($C_{3-6}$-alkynyloxy)carbonyl-$C_{1-4}$-alkyl, ($C_{3-8}$-cycloalkyloxy)carbonyl-$C_{1-4}$-alkyl, phenoxy-$C_{1-4}$-alkyl, $C_{3-6}$-alkenyloxy-$C_{1-4}$-alkyl, $C_{3-8}$-cycloalkenyloxy-$C_{1-4}$-alkyl, $C_{5-8}$-cycloalkenyl, $C_{6-8}$-bicycloalkyl, $C_{6-8}$-bicycloalkenyl, $C_{2-7}$-cyanoalkyl or $C_{3-6}$-alkynyloxy-$C_{1-4}$-alkyl,
$R^3$ signifies halogen or cyano,
$R^4$ signifies hydrogen or halogen,
$R^5$ signifies hydrogen, fluorine or $C_{1-4}$-alkyl and
$R^6$ signifies $C_{1-4}$-alkyl or $C_{1-4}$-haloalkyl or $R^5$ and $R^6$ together form trimethylene or tetramethylene, and the corresponding enol ethers of those compounds of formula I in which R is other than hydrogen or $C_{1-4}$-haloalkyl as well as Salts of those compounds of formula I in which $R^1$ signifies hydrogen.

Under the above-mentioned enol ethers there are thus to be understood the compounds of the formula

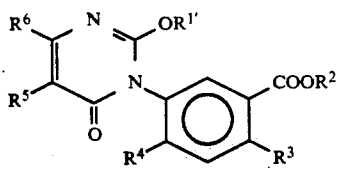
Ia wherein $R^{1'}$ signifies $C_{1-4}$-alkyl, $C_{3 \text{ or } 4}$-alkenyl or $C_{3 \text{ or } 4}$-alkynyl.

The compounds in accordance with the invention have herbicidal activity and are suitable as active ingredients of weed control compositions. Accordingly, the invention also embraces weed control compositions which contain compounds in accordance with the invention as the active ingredients, a process for the manufacture of these compounds as well as the use of the compounds or compositions for the control of weeds.

In formula I above "halogen" embraces fluorine, chlorine, bromine and iodine. The alkyl, alkenyl and alkynyl residues can be straight-chain or branched, and this also applies to the alkyl, alkenyl or alkynyl part of the haloalkyl, alkylsulphonylalkyl and other alkyl-, alkenyl- and, respectively. alkynyl-containing groups.

A haloalkyl group can have one or more (similar or different) halogen atoms.

The following are examples of residues $R^2$:
Acetylmethyl, 2-acetylethyl, propionylmethyl, cyanomethyl, trimethylsilylmethyl, 2-(trimethylsilyl)-ethyl, 2-(methylsulphonyl)-ethyl methoxycarbonylmethyl, ethoxycarbonylmethyl, 1-(methoxycarbonyl)-ethyl, 1-(ethoxycarbonyl)-ethyl, 1-(ethoxycarbonyl)-1-methylethyl, 2-(ethoxycarbonyl)-1-methylethyl, 2-phenoxyethyl, 2-cyclohexenyl, 2-cyanoethyl, 2-norbornanyl, 5-norbornen-2-yl, 2-allyloxyethyl and 2-propargyloxyethyl.

The salts of the compounds of formula I are especially alkali metal salts, e.g. sodium and potassium salts; alkaline earth metal salts, e.g. calcium and magnesium salts; ammonium salts, i.e. unsubstituted ammonium salts and mono- or polysubstituted ammonium salts, e.g. triethylammonium and methylammonium salts, as well as salts with other organic bases, e.g. with pyridine.

The presence of at least one asymmetric carbon atom in the compounds of formula I means that the compounds can occur in optically isomeric forms. Geometric isomerism can also occur when an aliphatic C=C double bond is present. Formula I is intended to embrace all of these possible isomeric forms as well as mixtures thereof.

When $R^1$ signifies $C_{3 \text{ or } 4}$-alkenyl. $C_{3 \text{ or } 4}$-alkynyl or $C_{1-4}$-haloalkyl, this residue is preferably allyl, propargyl or difluoromethyl, respectively. Where $R^6$ signifies haloalkyl, this is preferably trifluoromethyl or pentafluoroethyl. In general, a halogen atom which may be present is preferably fluorine, chlorine or bromine.

An interesting group of compounds in accordance with the invention comprises those compounds of formula I in which $R^2$ is other than carboxy-$C_{1-4}$-alkyl and $R^5$ signifies hydrogen. fluorine or $C_{1-4}$-alkyl and $R^6$ signifies $C_{1-4}$-alkyl or $C_{1-4}$-haloalkyl as well as their enol ethers and salts.

Independently of each other $R^1$ preferably signifies straight-chain $C_{1-4}$-alkyl, especially methyl; $R^2$ preferably signifies $C_{2-7}$-alkanoyl-$C_{1-4}$-alkyl. ($C_{1-6}$-alkoxy)carbonyl-$C_{1-4}$-alkyl. {[$C_{3-9}$-(α-alkylalkylidene)]iminooxy-($C_{1-6}$-alkoxy)carbonyl]-$C_{1-4}$-alkyl, ($C_{3-6}$-alkenyloxy)carbonyl-$C_{1-4}$-alkyl, ($C_{3-6}$-alkynyloxy)carbonyl-$C_{1-4}$-alkyl or ($C_{3-8}$cycloalkyloxy)carbonyl-$C_{1-4}$-alkyl; $R^3$ preferably signifies chlorine, bromine or cyano; $R^4$ preferably signifies hydrogen or fluorine; $R^5$ preferably signifies hydrogen, fluorine or methyl; and $R^6$ preferably signifies methyl. trifluoromethyl or pentafluoroethyl.

Preferred individual compounds of formula I are:
Ethyl 2-{2-chloro-5-[3,6-dihydro-3,4-dimethyl-2,6-dioxo-1(2H)-pyrimidinyl]-4-fluorobenzoyloxy}-2-methylpropionate.
methyl 2-{2-chloro-5-[3,6-dihydro-3,4-dimethyl-2,6-dioxo-1(2H)-pyrimidinyl]-4-fluorobenzoyloxy}-2-methylpropionate,
tert.butyl 2-{2-chloro-5-[3,6-dihydro-3,4-dimethyl-2,6-dioxo-1(2H)-pyrimidinyl]-4-fluorobenzoyloxy}-2-methyl-propionate,
ethyl 2-ethyl-2-{2-chloro-5-[3,6-dihydro-3,4-dimethyl-2,6-dioxo-1(2H)-pyrimidinyl]-4-fluorobenzoyloxy}-propionate,
methyl 2-{2-chloro-5-[3,6-dihydro-2,6-dioxo-3-methyl-4-trifluoromethyl-1(2H)-pyrimidinyl]-benzoyloxy}-2-methyl-propionate, isopropyl 2-{2-chloro-5-[3,6-dihydro-2,6-dioxo-3-methyl-4-trifluoromethyl-1(2H)-pyrimidinyl]-benzoyloxy}-propionate.

ethyl 2-ethyl-2-{2-chloro-5-[3,6-dihydro-2,6-dioxo-3-methyl-4-trifluoromethyl-1(2H)-pyrimidinyl]-benzoyloxy}-propionate, tert.butyl 2-{2-chloro-5-[3,6-dihydro-2,6-dioxo-3-methyl-4-trifluoromethyl-1(2H)-pyrimidinyl]-benzoyloxy-2-methyl-propionate.

allyl 2-{2-chloro-5-[3,6-dihydro-2,6-dioxo-3-methyl-4-trifluoromethyl-1(2H)-pyrimidinyl]-benzoyloxy}-2-methyl-propionate, cyclopentyl 2-{2-chloro-5-[3,6-dihydro-2,6-dioxo-3-methyl-4-trifluoromethyl-1(2H)-pyrimidinyl]-benzoyloxy}-2-methyl-propionate, ethyl 2-{2-chloro-5-[3,6-dihydro-2,6-dioxo-3-methyl-4-trifluoromethyl-1(2H)-pyrimidinyl]-benzoyloxy}-propionate, ethyl 2-{2-chloro-5-[3,6-dihydro-2,6-dioxo-3-methyl-4-trifluoromethyl-1(2H)-pyrimidinyl]-benzoyloxy}-2-methyl-propionate, 1-acetylethyl 2-chloro-5-[3,6-dihydro-2,6-dioxo-3-methyl 4-trifluoromethyl-1(2H)-pyrimidinyl]-benzoate and ethyl 3-{2-chloro-5-[3,6-dihydro-2,6-dioxo-3-methyl-4-trifluoromethyl-1(2H)-pyrimidinyl]-benzoyloxy]-butanoate.

The process in accordance with the invention for the manufacture of the compounds of formula I and of their enol ethers and salts comprises a) for the manufacture of those compounds of formula I in which $R^1$ signifies hydrogen as well as, if desired, of metal salts of these compounds, subjecting a compound of the general formula

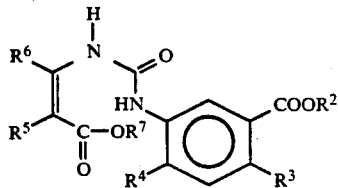

wherein $R^2$, $R^3$, $R^4$, $R^5$ and $R^6$ have the significances given above and $R^7$ signifies lower alkyl, preferably $C_{1-4}$-alkyl.

to a cyclization under basic conditions and, if desired, converting a metal salt of the uracil derivative of formula I which may be obtained into the acidic form ($R^1$=hydrogen) by treatment with an acid.

b) for the manufacture of those compounds of formula I in which $R^1$ signifies hydrogen and $R^6$ is other than $C_{1-4}$-haloalkyl as well as, if desired, of metal salts of these compounds, subjecting a compound of the general formula

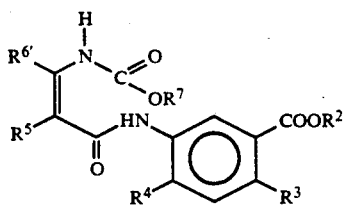

wherein $R^2$, $R^3$, $R^4$, $R^5$ and $R^7$ have the significances given above and $R^{6'}$ signifies $C_{1-4}$-alkyl or together with $R^5$ signifies trimethylene or tetramethylene, to a cyclization under basic conditions and, if desired, converting a metal salt of the uracil derivative of formula I which may be obtained into the acidic form ($R^1$=hydrogen) treatment with an acid.

c) for the manufacture of those compounds of formula I in which $R^1$ signifies $C_{1-4}$-alkyl. $C_{3\ or\ 4}$-alkenyl, $C_{3\ or\ 4}$-alkynyl or $C_{1-4}$-haloalkyl, subjecting a uracil derivative of the general formula

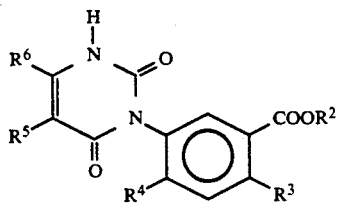

wherein $R^2$, $R^3$, $R^4$, $R^5$ and $R^6$ have the significances given above.

to an alkylation with an appropriate alkylating agent containing a $C_{1-4}$-alkyl, $C_{3\ or\ 4}$-alkenyl, $C_{3\ or\ 4}$-alkynyl or $C_{1-4}$-haloalkyl group.

d) for the manufacture of those compounds of formula I in which $R^1$ is other than hydrogen and of the corresponding enol ethers, esterifying a benzoic acid of the general formula

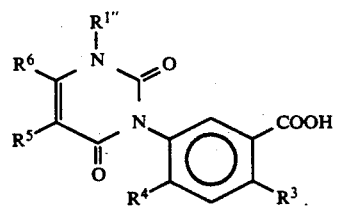

wherein $R^{1''}$ signifies $C_{1-4}$-alkyl, $C_{3\ or\ 4}$-alkenyl, $C_{3\ or}$ 4-alkynyl or $C_{1-4}$-haloalkyl and $R^3$, $R^4$, $R^5$ and $R^6$ have the significances given above, or the corresponding enol ether, where the benzoic acid or its enol ether can be present in the form of a reactive derivative, with a hydroxy compound of the general formula

wherein $R^2$ has the significance given above, or with a reactive derivative of this hydroxy compound, e) for the manufacture of those compounds of formula I in which $R^1$ is other than hydrogen, subjecting a benzoic acid ester of the general formula

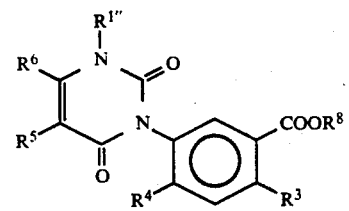

wherein $R^{1''}$, $R^3$, $R^4$, $R^5$ and $R^6$ have the significances given above and $R^8$ signifies $C_{2-6}$-alkoxyalkyl, to a trans-esterification reaction with a hydroxy compound of formula V given above, where the reagent V has a higher boiling point than the alkanol, alkenol or alkynol $R^8OH$.

f) for the manufacture of those compounds of formula I in which $R^3$ signifies cyano and of the corresponding enol ethers, treating a 2-halo-benzoate of the general formula

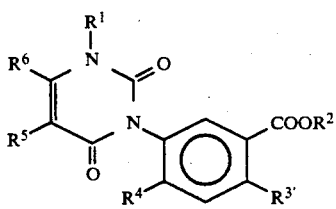
I'' wherein $R^{3'}$ signifies halogen, preferably chlorine or bromine and $R^1$, $R^2$, $R^4$, $R^5$ and $R^6$ have the significances given above,
or the corresponding enol ether with a metal cyanide.

g) for the manufacture of the enol ethers of the compounds of formula I, treating a uracil derivative of the general formula

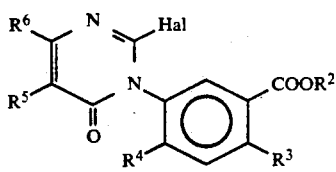
VII wherein $R^2$, $R^3$, $R^4$, $R^5$ and $R^6$ have the significances given above and Hal signifies chlorine or bromine,
with an alkanol, alkenol or alkynol $R^{1'}OH$ in the presence of an organic base or with the corresponding alcoholate, alkenolate or alkynolate of the general formula $$R^{1'}L^{\ominus}M^{\oplus} \qquad VIII$$

wherein $R^{1'}$ has the significance given above and $M^{\oplus}$ signifies one equivalent of a metal ion.
and, if desired, converting a thus-obtained compound of formula I in which $R^1$ signifies hydrogen into a salt.

The cyclization according to process variant a) or b) can be carried out conveniently by treating the compound of formula II or III in an inert protic organic solvent such as an alcohol. e.g. methanol, ethanol or isopropanol; an inert aprotic organic solvent such as an aliphatic or cyclic ether, e.g. 1,2-dimethoxyethane, tetrahydrofuran or dioxan, or an aromatic, e.g. benzene or toluene; an inert aprotic polar organic solvent, e.g. dimethylformamide or dimethyl sulphoxide, where such solvents can be used, if desired, in a two-phase mixture with a hydrocarbon, e.g. n-hexane or toluene; or water with a base at temperatures between $-78°$ C. and the reflux temperature of the reaction mixture. As bases there preferably come into consideration sodium alcoholates, alkali metal hydroxides, especially sodium hydroxide and potassium hydroxide, alkali metal carbonates, especially sodium carbonate and potassium carbonate, and sodium hydride. When an alkanol is used as the solvent, this solvent conveniently corresponds to the respective hydroxy compound $R^2$—OH; thereby undesired competing trans-esterification reactions are avoided. When sodium hydride is used as the base, the solvent is preferably an aliphatic or cyclic ether, dimethylformamide or dimethyl sulphoxide, where any of these solvents can be used in admixture with toluene.

After completion of the cyclization the product, when one of the above-mentioned bases or the like is used, is present in the form of the corresponding alkali metal salt. This can be isolated and purified in a manner known per se or the mixture can be acidified in order to isolate the respective compound of formula I itself. A mineral acid such as hydrochloric acid or a strong organic acid such as acetic acid or p-toluenesulphonic acid is preferably used for this purpose.

In process variant c) the term "alkylation" refers to the substitution of the hydrogen atom of the $N^1$-atom of the uracil nucleus with a $C_{1-4}$-alkyl, $C_{3\,or\,4}$-alkenyl, $C_{3\,or\,4}$-alkynyl or $C_{1-4}$-haloalkyl group. As the alkylating agent there is conveniently used a $C_{1-4}$-alkyl, $C_{3\,or\,4}$-alkenyl or $C_{3\,or\,4}$-alkynyl halide, especially the respective chloride or bromide, or sulphate or a multiply halogenated $C_{1-4}$-alkane such as, for example. chlorodifluoromethane or a mono- or multiply halogenated alkene such as, for example, tetrafluoroethene.

The alkylation is conveniently carried out in the presence of an inert, protic organic solvent such as a lower alkanol, e.g. ethanol, optionally in admixture with water; an inert, aprotic organic solvent such as an aliphatic or cyclic ether, e.g. 1,2-dimethoxyethane, tetrahydrofuran or dioxan; a ketone, e.g. acetone or butan-2-one; or an inert, aprotic, polar organic solvent, e.g. dimethylformamide, dimethyl sulphoxide or acetonitrile, as well as in the presence of a base such as sodium hydride, an alkali metal hydroxide, especially sodium hydroxide or potassium hydroxide, an alkali metal alcoholate, especially sodium alcoholate, or an alkali metal carbonate or bicarbonate, especially sodium carbonate, potassium carbonate, sodium bicarbonate or potassium bicarbonate, at temperatures between $0°$ C. and the reflux temperature of the reaction mixture, preferably at room temperature or, in the case of the substitution of the hydrogen atom of the $N^1$-atom with a $C_{1-4}$-haloalkyl group, preferably at temperatures between $50°$ C. and $100°$ C. In a preferred embodiment, the uracil derivative of formula I' is treated firstly with the base such as sodium hydride, sodium ethanolate or sodium carbonate, in the solvent and, after a short reaction time, with the halide in the same solvent. In a further embodiment, the uracil derivative I' is reacted with a dialkyl sulphate in the presence of an alkali metal bicarbonate, especially sodium bicarbonate or potassium bicarbonate, in the solvent, e.g. acetone, at reflux temperature. Depending on the solvent which is used, the reaction has generally finished within a relatively short time or after a few hours.

Process variant d) is an esterification of the benzoic acid or of the enol ether or of a reactive derivative thereof, which can be carried out according to methods known per se. Thus, for example, a salt of a benzoic acid of formula IV or of the corresponding enol ether is reacted with a halide, especially chloride, bromide or iodide, or the sulphate, mesylate or tosylate of the hydroxy compound V in an inert diluent at temperatures between room temperature and $100°$ C., e.g. at the reflux temperature of the reaction mixture, preferably in the temperature range of $40°$ C. to $70°$ C. As salts of the benzoic acid of formula IV or of the corresponding enol ether there especially come into consideration alkali metal salts, e.g. the sodium, potassium or lithium salt, alkaline earth metal salts, e.g. the magnesium, calcium or barium salt, and salts with organic bases such as tertiary amines, e.g. triethylamine, 1,5-diaza-bicyclo[4.3.0]non-5-ene, 1,8-diaza-bicyclo[5.4.0]undec-7-ene and 1,4-diazabicyclo [2.2.2]octane, with the alkali metal salts, especially the sodium salt and the potassium salt, being preferred. The diluents which can be used are preferably inert organic solvents such as lower alkanols, e.g. ethanol, aliphatic and cyclic ethers, e.g. diethyl ether, tetrahydrofuran and dioxan, ketones, e.g. acetone and 2-butanone, dimethylformamide, dimethyl sulphoxide, acetonitrile and hexamethylphosphoric acid triamide. The salt can be produced in situ by converting the acid with a suitable inorganic base, e.g. an alkali metal or alkaline earth metal carbonate, bicarbonate, hydroxide or hydride, or organic base into the salt and subsequently reacting this in the same reaction medium with the second reaction partner.

When an acid halide of the benzoic acid of formula IV or of the corresponding enol ether is used as the reactive derivative, this is conveniently reacted with the hydroxy compound of formula V in an inert organic solvent such as an aliphatic or cyclic ethet, e.g. diethyl ether, 1,2-dimethoxyethane, tetrahydrofuran or dioxan, an aliphatic or aromatic hydrocarbon, e.g. n-hexane, benzene or toluene, or a halogenated, especially chlorinated, hydrocarbon, e.g. methylene chloride, chloroform or carbon tetrachloride, at temperatures from about $-20°$ C. to $100°$ C., preferably from $0°$ C. to $50°$ C. Moreover, the reaction is conveniently carried out in the presence of an acid-binding agent such as an organic base, e.g. triethylamine, pyridine, 4-dimethylaminopyridine, 1,5-diaza-bicyclo-[4.3.0]non-5-ene, 1,8-diaza-bicyclo[5.4.0]undec-7-ene or 1,4-diaza-bicyclo(2.2.2)octane. The acid halide is preferably the acid chloride.

As further reactive derivatives of the benzoic acid of formula IV or of the corresponding enol ether which come into consideration there can be named the corresponding O-acyl-1,3-dicyclohexylisourea and the corresponding N-acylimidazole or acid anhydride. Such derivatives can be reacted like the acid halide with the hydroxy compounds of formula V in order to proceed to the desired benzoic acid esters. In these cases, however, the use of an acid-binding agent is unnecessary.

The reaction according to process variant e) can be carried out conveniently by heating the benzoic acid ester of formula VI in excess hydroxy compound of formula V in the presence of a basic catalyst such as sodium cyanide, preferably at the reflux temperature of the reaction mixture. In the course of the reaction the residue $R^8$ of the benzoic acid ester VI is replaced by the group $R^2$ of the hydroxy compound V, with the alkanol, alkenol or alkynol $R^8OH$ which has a lower boiling point being liberated.

Process variant f) is an exchange reaction of the halogen substituent on the benzene nucleus. Thus, this halogen atom is replaced by the cyano group using the metal cyanide. The latter is especially a transition metal cyanide, preferably copper(I) cyanide. The reaction is conveniently effected in the presence of an aprotic, polar solvent such as an alkyl nitrile, e.g. acetonitrile, propionitrile or butyronitrile: an alkylurea, e.g. N,N,N',N'-tetramethylurea; a dialkylamide, e.g. dimethylformamide; a dialkyl sulphoxide, e.g. dimethyl sulphoxide; N-methyl-2-pyrrolidone; 1,3-dimethyl-imidazolidin-2-one; 1,3-dimethyl-3,4,5,6-tetrahydro-2(1H)-pyrimidinone; or hexamethylphosphoric acid triamide, at elevated temperatures, namely between $150°$ C. and $250°$ C. $R^4$ in the starting material I" preferably signifies hydrogen or fluorine.

In process variant g) the term "metal ion" stands especially for an alkali metal ion, e.g. the sodium or potassium ion, or an alkaline earth metal ion, e.g. the calcium or magnesium ion. The sodium ion is the preferred metal ion. Where the alkanol, alkenol or alkynol $R^1OH$ is used, pyridine is the especially suitable organic base.

The reaction is conveniently effected in an excess of the corresponding alcohol $R^1OH$ as the diluent and at temperatures between $0°$ C. and $50°$ C., preferably at room temperature.

Insofar as they are not manufactured directly by the above-described cyclization which is carried out under basic conditions, the desired salts of the compounds of formula I in which $R^1$ signifies hydrogen can also be manufactured from these compounds I in a manner known per se such as, for example, by dissolving the compound of formula I in a solution of a respective inorganic or organic base. The salt formation is generally effected within a short time at room temperature. In one embodiment the sodium salt is manufactured by dissolving the uracil derivative I in aqueous sodium hydroxide solution at room temperature, with equivalent amounts of the uracil derivative and of sodium hydroxide being used. The solid salt can then be isolated by precipitation with a suitable inert solvent or by evaporation of the solvent. A further embodiment comprises introducing an aqueous solution of an alkali metal salt of the uracil derivative I into an aqueous solution of a salt which has a metal ion other than an alkali metal ion, in which case the second metal salt of the uracil derivative is manufactured. This embodiment is generally used for the manufacture of uracil metal salts which are insoluble in water.

The resulting compounds of formula I, enol ethers as well as salts can be isolated and purified according to methods known per se. Further, the sequence in which possible combinations of process variants c) to f) will be conveniently carried out in order to avoid possible undesirable competing reactions will be familiar to a person skilled in the art.

Insofar as no planned synthesis for the isolation of pure isomers is carried out, the product can result as a mixture of two or more isomers. The isomers can be separated according to methods known per se. If desired, pure optically active isomers,for example, can also be manufactured by synthesis from corresponding optically active starting materials.

The starting materials of formula II, which are novel, can be produced in a manner known per se, e.g. in accordance with the following Reaction Schemes 1 [methods aa), bb) and cc)]:

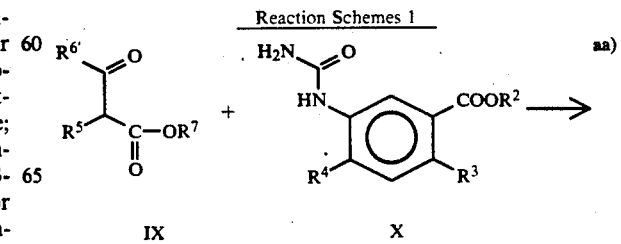

-continued
Reaction Schemes 1

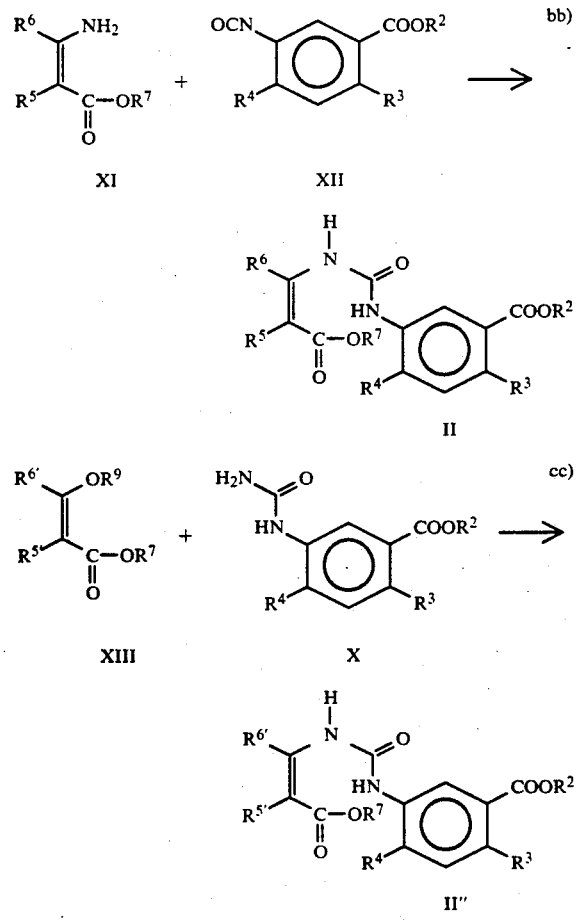

In the above reaction schemes $R^2$, $R^3$, $R^4$, $R^5$, $R^6$, $R^{6'}$ and $R^7$ have the significances given above; $R^{5'}$ signifies hydrogen or $C_{1-4}$-alkyl; or together with $R^{6'}$ signifies trimethylene or tetramethylene; and $R^9$ signifies lower alkyl, preferably $C_{1-4}$-alkyl.

Method aa) is conveniently carried out by reacting the compounds of formulae IX and X with each other in an essentially anhydrous diluent and in the presence of an acidic catalyst at an elevated temperature. As diluents there especially come into consideration organic solvents which form azeotropes with water, such as aromatics, e.g. benzene, toluene and xylenes; halogenated hydrocarbons such as methylene chloride, chloroform, carbon tetrachloride and chlorobenzene: and aliphatic and cyclic ethers such as 1,2-dimethoxyethane, tetrahydrofuran and dioxan, and as acidic catalysts there especially come into consideration strong mineral acids such as sulphuric acid and hydrochloric acid; organic acids such as p-toluenesulphonic acid; phosphorus-containing acids such as orthophosphoric acid and polyphosphoric acid; and acidic cation exchangers such as "Amberlyst 15" (Fluka). The reaction is generally carried out in a temperature range of about 70° C. to 120° C., preferably at the reflux temperature of the reaction mixture. Under these reaction conditions the desired rapid removal of the water which is formed in the reaction is achieved.

The reaction according to method bb) is conveniently effected in the presence of an essentially anhydrous aprotic organic solvent such as an aliphatic or cyclic ether, e.g. diethyl ether, 1,2-dimethoxyethane, tetrahydrofuran or dioxan, an aliphatic or aromatic hydrocarbon, e.g. n-hexane, benzene, toluene or a xylene; or a halogenated, aliphatic hydrocarbon, e.g. methylene chloride, chloroform, carbon tetrachloride or 1,2-dichloroethane, as well as optionally in the presence of a base, especially an organic tertiary base such as triethylamine or pyridine, where the latter can serve not only as the solvent but also as the base, or a metal hydride such as sodium hydride or potassium hydride. The reaction temperatures are preferably in the range of about −80° C. to 50° C., with the reaction being carried out particularly preferably at temperatures between −30° C. and room temperature.

The reaction according to method cc) is conveniently carried out in an inert, water-miscible, organic solvent such as an aliphatic or cyclic ether, e.g. 1,2-dimethoxyethane, tetrahydrofuran or dioxan, or a lower alkanol such as ethanol at temperatures between 50° C. and 100° C., preferably at the reflux temperature of the reaction mixture, or in an aromatic solvent such as benzene, toluene or a xylene in the presence of an acidic catalyst such as hydrochloric acid or p-toluenesulphonic acid at temperatures between 50° C. and 100° C., preferably 60° C. to 80° C.

The starting materials of formula III are also novel and can be produced in a manner known per se, e.g. in accordance with the following Reaction Schemes 2 [methods dd), ee) and ff)]:

Reaction Schemes 2

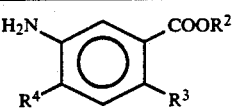
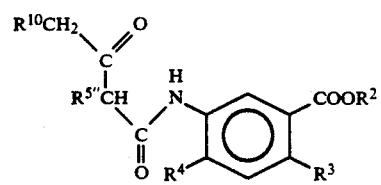
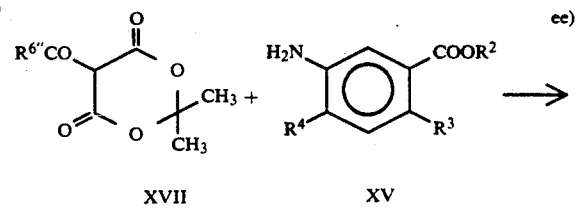

-continued
Reaction Schemes 2

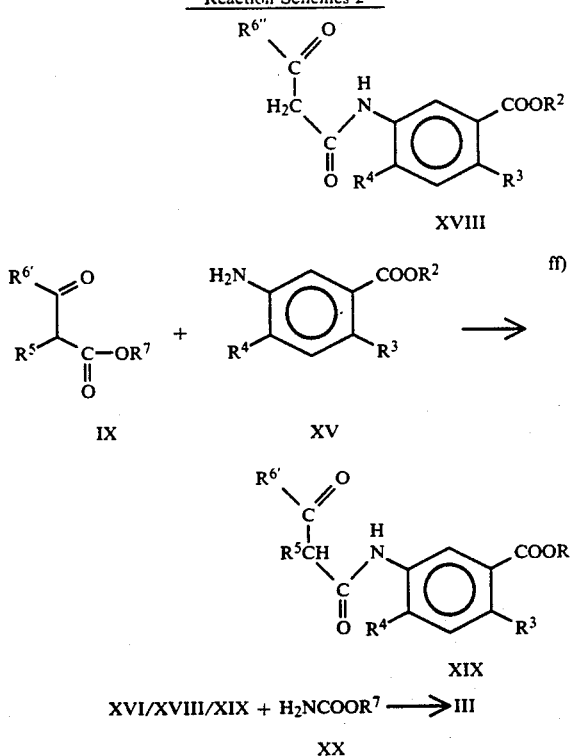

XVI/XVIII/XIX + H$_2$NCOOR$^7$ ⟶ III

XX

In the above reaction schemes R$^2$, R$^3$, R$^4$, R$^5$, R$^{6'}$ and R$^7$ have the significances given above; R$^{5''}$ signifies hydrogen or C$_{1-4}$-alkyl; R$^{6''}$ signifies C$_{1-4}$-alkyl; and R$^{10}$ signifies hydrogen or C$_{1-3}$-alkyl.

The reaction of the amine of formula XV with the diketene of formula XIV according to method dd) is conveniently effected in an anhydrous inert aprotic solvent such as a halogenated hydrocarbon, e.g. methylene chloride, chloroform, carbon tetrachloride or chlorobenzene, an aromatic hydrocarbon, e.g. benzene, toluene or a xylene, or an aliphatic or cyclic ether, e.g. diethyl ether, 1,2-dimethoxyethane, tetrahydrofuran or dioxan, in the presence of a basic catalyst such as 4-pyrrolidinopyridine, 4-dimethylaminopyridine, 1,4-diazabicyclo[2,2,2]octane, 1,5-diazabicyclo[4,3,0]non-5-ene, 1,8-diazabicyclo[5,4,0]undec-7-ene or diethylamine. Since the reaction is exothermic, it is generally carried out in a temperature range of −10° C. to 50° C., preferably at room temperature.

The reaction of the compounds of formulae XVII and XV with each other according to method ee) is conveniently carried out in an anhydrous, inert, aprotic solvent at temperatures from about 70° C. to 140° C. Preferably from 100° C. to 120° C. As such solvents there are especially suitable aromatics, e.g. benzene, toluene and xylenes; halogenated hydrocarbons, e.g. carbon tetrachloride, trichloroethane, tetrachloroethane and chlorobenzene; and aliphatic and cyclic ethers, e.g. dibutyl ether, 1,2-dimethoxyethane, tetrahydrofuran and dioxan.

The reaction according to method ff) is an aminolysis which is conveniently effected in an anhydrous solvent or in the absence of a solvent [see, for example, J. Soc. Dyes Col. 42, 81 (1926), Ber. 64, 970 (1931) and J.A.C.S. 70, 2402 (1948)] at an elevated temperature. As solvents here especially come into consideration inert, aprotic solvents such as optionally halogenated aromatics, e.g. toluene, xylenes and chlorobenzenes. The reaction is generally carried out in a temperature range from about 130° C. to 160° C., If desired, the reaction is, moreover, carried out in the presence of a basic catalyst, e.g. a high-boiling amine [see, or example, Helv. Chim. Acta 11, 779 (1928) and U.S. Pat. No. 2,416,738] or pyridine.

The subsequent reaction of the thus-produced compound of formula XVI, XVIII or XIX with the lower alkyl carbamate of formula XX is conveniently effected in an essentially anhydrous diluent and in the presence of an acidic catalyst at an elevated temperature. As diluents there especially come into consideration organic solvents which form azeotropes with water, such as aromatics, e.g. benzene, toluene and xylenes; and halogenated hydrocarbons such as carbon tetrachloride and chlorobenzene, and as acidic catalysts there especially come into consideration strong mineral acids such as sulphuric acid; organic acids such as p-toluenesulphonic acid; phosphorus-containing acids such as orthophosphoric acid and polyphosphoric acid; and acidic cation exchangers such as "Amberlyst 15" (Fluka). The reaction is generally carried out in a temperature range of about 70° C. to 150° C. preferably at the reflux temperature of the reaction mixture. Under these reaction conditions the desired rapid removal of the water which is formed in the reaction is achieved.

The starting materials of formulae IV and VI and their production are for the most part described in European Patent Publication No. 195,346. Those starting materials IV and VI whose production is not described can be produced analogously to the known starting materials. The reactive derivatives of the benzoic acids of formula IV, which can likewise be used as starting materials, can be produced from these benzoic acids according to methods known per se. The enol ethers of the benzoic acids IV, i.e. the compounds of the general formula

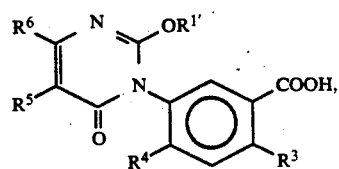

IVa which can also be used as starting materials in process variant d), are described in International (PCT) Patent Publication No. WO 88/10254.

The starting materials of formula VII which are used in process variant g) can be produced by halogenating the corresponding uracil derivatives of formula I' given above. In this halogenation there is used as the halogenating agent especially thionyl chloride, phosphorus pentachloride or phosphorus oxychloride or, respectively, phosphorus pentabromide or phosphoryl bromide. If desired, a mixture of phosphorus pentachloride and phosphorus oxychloride or of phosphorus pentabromide and phosphoryl bromide can be used, in which case an excess of phosphorus oxychloride or phosphoryl bromide can serve as the diluent. The chlorination or bromination can be carried out in the presence of an inert diluent, especially an aprotic organic solvent such as an aliphatic or aromatic hydrocarbon, e.g. n-hexane, benzene, toluene or a xylene; a halogenated aliphatic hydrocarbon, e.g. methylene chloride, chloroform or 1,2-dichloroethane; a halogenated aromatic hydrocarbon, e.g. chlorobenzene, or a tertiary amine, e.g. N,N-dimethylaniline, but this is not necessary when phosphorus oxychloride or phosphoryl bromide is used as the halogenating agent. When thionyl chloride is used as the halogenating agent, it has been found to be convenient to add a catalytic amount of dimethylformamide. The reaction temperatures generally lie between 0° C. and the reflux temperature of the reaction mixture, preferably between 80° C. and 120° C.

The uracil derivatives of formula I' and I" which are used as starting materials in process variants c) and f), respectively, are sub-groups of compounds of formula I. The remaining starting materials and, respectively, reagents which are involved in process variants d), f) and g) as well as in Reaction Schemes 1 and 2 are either known or can be produced according to methods known per se.

The compounds of formula I as well as their enol ethers or salts are suitable for controlling, for preventing or for destroying plant growth, especially undesired plant growth. The compounds have in particular herbicidal properties and are suitable for the control of weeds, including weed grasses, for example *Abutilon theophrasti, Amaranthus retroflexus, Cassia obtusifolia, Chenopodium album, Chyrsanthemum segetum, Datura stramonium, Digitaria sanguinalis, Echinochloa crusgalli, Galium aparine, Matricaria chamomilla, Setaria faberii, Sinapis arvensis* and *Xanthium Pennsylvanicum,* in diverse crops, for example cape, soya, cotton, rice, wheat and maize crops. Moreover, the compounds are not only pre-emergence but also post-emergence herbicides. Furthermore, the compounds can be used for the control of undesired plant growth, e.g. in potatoes cotton, sunflowers and aquatic weeds. They can be used, for example, as desiccants for facilitating the harvesting in the case of potatoes and cotton.

In practice, a concentration of 1 g to 3 kg of compound in accordance with the invention/ha, preferably 10 g to 1 kg of compound in accordance with the invention/ha, is usually sufficient to achieve the desired herbicidal effect. The concentration range 15 to 500 g of compound in accordance with the invention/ha is especially preferred.

The weed control composition in accordance with the invention contains an effective amount of at least one compound of formula I, as defined above, or an enol ether or salt thereof as well as formulation adjuvants. The composition conveniently contains at least one of the following formulation adjuvants: solid carrier substances; solvents or dispersion media; surfactants(wetting and emulsifying agents); dispersing agents (without surfactant action); and stabilizers. With the use of these and other adjuvants these compounds, namely the herbicidal active substances, can be converted into the usual formulations such as dusts, powders, granulates, solutions, emulsions, suspensions, emulsifiable concentrates, pastes and the like.

The compounds of formula I and their enol ethers are generally insoluble in water, whereas the salts, especially the alkali metal salts and ammonium salts, are generally soluble in water, and can be formulated according to methods which are usual for water-insoluble or water-soluble compounds using the respective formulation adjuvants. The manufacture of the compositions can be carried out in a manner known per se, e.g. by mixing the respective active ingredient with solid carrier substances, by dissolution or suspension in suitable solvents or dispersion media, if necessary using surfactants as wetting or emulsifying agents and/or dispersing agents, by diluting pre-prepared emulsifiable concentrates with solvents or dispersion media etc.

As solid carrier substances there essentially come into consideration: natural mineral substances such as chalk, dolomite, limestone, aluminas and silicic acid and salts thereof (for example siliceous earth, kaolin, bentonite, talc, attapulgite and montmorillonite); synthetic mineral substances such as highly disperse silicic acid, aluminium oxide and silicates; organic substances such as cellulose, starch, urea and synthetic resins; and fertilizers such as phosphates and nitrates, where such carrier substances can be present e.g. as powders or as granulates.

As solvents or dispersion media there essentially come into consideration: aromatics such as benzene, toluene, xylenes and alkylnaphthalenes: chlorinated aromatics and chlorinated aliphatic hydrocarbons such as chlorobenzenes, chloroethylenes and methylene chloride; aliphatic hydrocarbons such as cyclohexane and paraffins, e.g. petroleum fracrions; alcohols such as butanol and glycol, as well as their ethers and esters; ketones such as acetone, methyl ethyl ketone, methyl isobutyl ketone and cyclohexanone; and strongly polar solvents or dispersion media such as dimethylformamide, N-methylpyrrolidone and dimethyl sulphoxide, such solvents preferably having flash points of at least 30° C. and boiling points of at least 50° C., and water. Among the solvents or dispersion media there also come into consideration so-called liquefied gaseous extenders or carrier substances, which are those products which are gaseous at room temperature and under normal pressure. Examples of such products are especially aerosol propellants such as hydrocarbons, e.g. propane and isobutane, and halogenated hydrocarbons, e.g. dichlorodifluoromethane. If the weed control composition in accordance with the invention is present in the form of a pressurized pack, then a solvent is conveniently used in addition to the propellant.

The surfactants (wetting and emulsifying agents) can be non-ionic compounds such as condensation products of fatty acids, fatty alcohols or fatty-substituted phenols with ethylene oxide; fatty acid esters and ethers of sugars or polyvalent alcohols; the products which are obtained from sugars or polyvalent alcohols by condensation with ethylene oxide: block polymers of ethylene oxide and propylene oxide; or alkyldimethylamine oxides.

The tensides can also be anionic compounds such as soaps; fatty sulphate esters, e.q. dodecyl sodium sulphate, octadecyl sodium sulphate and cetyl sodium sulphate; alkylsulphonates, arylsulphonates and fatty-aromatic-sulphonates such as alkylbenzenesulphonates, e.q. calcium dodecylbenzenesulphonate, and butyl naphthalenesuophonates; and more complex fatty sulphonates, e.g. the amide condensation products of oleic acid and N-methyltaurine and the sodium sulphonate of dioctyl succinate.

Finally, the surfactants can be cationic compounds such as alkyldimethylbenzylammonium chlorides, dialkyldimethylammonium chlorides, alkyltrimethylammonium chlorides and ethoxylated quaternary ammonium chlorides.

As dispersing agents (without surfactant action) there essentially come into consideration; lignin, sodium and ammonium salts of ligninsulphonic acids, sodium salts of maleic anhydride-diisobutylene copolymers, sodium and ammonium salts of sulphonated polycondensation products of naphthalene and formaldehyde, and sulphite lyes.

As dispersing agents, which are especially suitable as thickening or anti-settling agents, there can be used e.g. methylcellulose, carboxymethylcellulose, hydroxyethylcellulose, polyvinyl alcohol, alginates, caseinates and blood albumin.

Examples of suitable stabilizers are acid-binding agents, e.g. epichlorohydrin, phenyl glycidyl ether and soya epoxides: antioxidants, e.g. gallic acid esters and butylhydroxytoluene; UV-absorbers, e.g. substituted benzophenones, diphenylacrylonitrile acid esters and cinnamic acid esters; and deactivatots, e.g. salts of ethylenediaminotetraacetic acid and polyglycols.

The weed control compositions in accordance with the invention can contain, in addition to the active ingredients in accordance with the invention, synergists and other active ingredients, e.g. insecticides, acaricides, fungicides, plant growth regulators and fertilizers. Such combination compositions are suitable for intensifying the activity or for broadening the spectrum of activity.

The weed control compositions in accordance with the invention generally contain between 0.001 and 95 weight percent, preferably between 0.5 and 75 weight percent, of one or more compounds in accordance with the invention as the active ingredient(s). They can be present e.g. in a form which is suitable for storage and transport. In such formulations, e.g. emulsifiable concentrates, the active ingredient concentration is normally in the higher range, preferably between 1 and 50 weight percent, especially between 10 and 30 weight percent. These formulations can then be diluted, e.g. with the same or different inert substances, to give active ingredient concentrations which are suitable for practical use, i.e. preferably about 0.001 to 10 weight percent, especially about 0.005 to 5 weight percent. The active ingredient concentrations can, however, also be smaller or greater.

As mentioned above, the manufacture of the weed control compositions in accordance with the invention can be carried out in a manner known per se.

For the manufacture of pulverulent preparations the active ingredient, i.e. at least one compound in accordance with the invention, can be mixed with a solid carrier substance, e.g. by grinding together; or the solid carrier substance can be impregnated with a solution or suspension of the active ingredient and then the solvent or dispersion medium can be removed by evaporation, heating or sucking-off under reduced pressure. By adding surfactants or dispersing agents such pulverulent preparations can be made readily wettable with water, so that they can be converted into aqueous suspensions which are suitable e.g. as spray compositions.

The active ingredient can also be mixed with a surfactant and a solid carrier substance to form a wettable powder which is dispersible in water, or it can be mixed with a solid pre-granulated carrier substance to form a product in the form of a granulate.

When desired, the active ingredient can be dissolved in a water-immiscible solvent such as, for example, a high-boiling hydrocarbon, which conveniently contains dissolved emulsifying agent so that the solution becomes self-emulsifying upon addition to water. Alternatively, the active ingredient can be mixed with an emulsifying agent and the mixture can then be diluted with water to the desired concentration. Moreover, the active ingredient can be dissolved in a solvent and thereafter the solution can be mixed with an emulsifying agent. Such a mixture can likewise be diluted with water to the desired concentration. In this manner there are obtained emulsifiable concentrates or ready-for-use emulsions.

The use of the weed control compositions in accordance with the invention, which forms a further subject of the present invention, can be carried out according to usual application methods such as sprinkling, spraying, dusting, watering or scattering. The method in accordance with the invention for the control of weeds comprises treating the locus to be protected against weeds and/or the weeds with a compound in accordance with the invention or with a weed control composition in accordance with the invention.

The following Examples serve to illustrate the invention in more detail.

I. Manufacture of the active ingredients of formula I:

EXAMPLE 1

2.5 g of 2-chloro-5-[3,6-dihydro-2,6-dioxo-3-methyl-4-trifluoromethyl-1(2H)-pyrimidinyl]-4-fluorobenzoic acid are heated to reflux temperature for 3 hours in 20 ml of benzene and 2.9 ml of thionyl chloride together with 2 drops of dimethylformamide. Subsequently, the reaction mixture is evaporated to dryness and dissolved in 20 ml of dioxan. This solution, which consists mainly of the acid chloride of the above-mentioned benzoic acid and the solvent, is added dropwise to a solution of 0.8 ml of methyl D,L-lactate and 1.0 g of pyridine in 10 ml of dioxan. Then, the reaction mixture is stirred at room temperature for 3 hours, treated with 400 ml of water and extracted twice with 400 ml of ethyl acetate each time. The combined organic phases are washed twice with 200 ml of hydrochloric acid each time and once with 200 ml of saturated sodium chloride solution, dried over anhydrous sodium sulphate and evaporated. The residue is purified by chromatography on silica gel with ethyl acetate/n-hexane (1:4). In this flacunal there is obtained methyl 2-{2-chloro-5-[3,6-dihydro-2,6-dioxo-3-methyl-4-trifluoromethyl-1(2H)-pyrimidinyl]-4-fluorobenzoyloxy}-propionate which can be recrystallized from ethyl acetate/n-hexane; m.p. 102°–104° C.

EXAMPLES 2–10

The compounds of formula I listed in Table 1 hereinafter are obtained analogously to the procedure described in Example 1 starting from 2-chloro-5-[3,6-dihydro-2,6-dioxo-3-methyl-4-trifluoromethyl-1(2H)-pyrimidinyl]-4-fluorobenzoic acid via its acid chloride:

TABLE 1

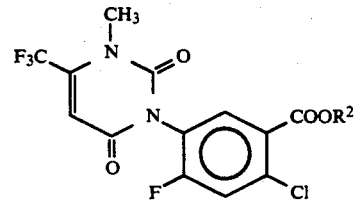

| Example | R² | Physical data |
|---|---|---|
| 2 | Acetylmethyl | Oil; $^1$H—NMR (d$_6$-DMSO), 400 MHz): 2.17 ppm (s,3H), 3.42 ppm (s,3H), 5.07 ppm (s,2H), 6.60 ppm (s,1H), 7.92 ppm (d,1H), 8.15 ppm (d,1H); |

TABLE 1-continued

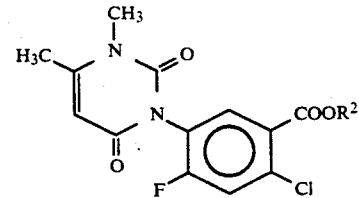

| Example | R² | Physical data |
|---|---|---|
|  |  | mass spectrum (m/e): 422(18) M⁺ |
| 3 | 1-Acetylethyl | Oil; ¹H—NMR (d₆-DMSO, 400 MHz): 1.48 ppm (d,3H), 2.22 ppm (s,3H), 3.43 ppm (s,3H), 5.36 ppm (dq,1H), 6.61 ppm (d,1H), 7.92 ppm (d,1H), 8.14 ppm (d,1H), |
| 4 | Trimethylsilylmethyl | Oil; ¹H—NMR (d₆-DMSO, 400 MHz): 0.11 ppm (s,9H), 3.42 ppm (s,3H), 4.06 ppm (s,2H), 6.61 ppm (s,1H), 7.88 ppm (d,1H), 7.99 ppm (d,1H) |
| 5 | 2-(Trimethylsilyl)-ethyl | Oil; ¹H—NMR (d₆-DMSO, 400 MHz): 0.05–0.07 ppm (m,9H), 1.08–1.14 ppm (m,2H), 3.43 ppm (s,3H), 4.37–4.43 ppm (m,2H), 6.61 ppm (s,1H), 7.88 ppm (d,1H), 8.05 ppm (d,1H), |
| 6 | 2-(Methylsulphonyl)-ethyl | M.p. 140–142° C. |
| 7 | 2-Phenoxyethyl | M.p. 98–100° C. |
| 8 | 2-Cyclohexenyl | Oil; ¹H—NMR (d₆-DMSO, 400 MHz): 1.56–2.12 ppm (m,6H), 3.42 ppm (s,3H), 5.40–5.46 ppm (m,1H), 5.76–5.84 ppm (m,1H), 6.00–6.07 ppm (m,1H), 6.61 ppm (s,1H). 7.88 ppm (d,1H), 8.02 ppm (d,1H) |
| 9 | Cyanomethyl | M.p. 113–115° C. |
| 10 | [(1R,5S)-6,6-Dimethyl-2-norpinen-2-yl]-methyl | ¹H—NMR (d₆-DMSO, 400 MHz): 0.80 ppm (s,3H), 1.13 ppm (d,1H), 1.26 ppm (s,3H), 2.06–2.12 ppm (m,1H), 2:16–2.25 ppm (m,2H), 2.26–2.36 ppm (m,1H), 2.37–2.44 ppm (m,1H), 3.53 ppm (s,broad,3H), 4.66–4.77 ppm (m,2H), 5.65–5.70 ppm (m,1H), 6.60 ppm (s,1H), 7.88 ppm (d,1H), 8.03 ppm (d,1H); [α]$_D^{20}$ = −12.0° (CHCl₃. c = 0.4%) |

EXAMPLES 11–40

The compounds of formula I listed in Table 2 hereinafter were obtained analogously to the procedure described in Example 1 starting from 2-chloro-5-[3,6-dihydro-3,4-dimethyl-2,6-dioxo-1(2H)-pyrimidinyl]-4-fluorobenzoic acid via its acid chloride:

TABLE 2

| Example | R² | Physical data |
|---|---|---|
| 11 | 2-Cyclohexenyl | Oil; ¹H—NMR (d₆-DMSO, 400 MHz): 1.56–2.14 ppm (m,6H), 2.33 ppm (s,3H), 3.36 ppm (s,3H), 5.42 ppm (m,1H), 5.80 ppm (m,2H), 6.02 (m,1H), 7.82 ppm (d,1H), 7.92 (d,1H); mass spectrum (m/e): 392(15) M⁺ |
| 12 | Propionylmethyl | Oil; ¹H—NMR (d₆-DMSO, 400 MHz): 0.98 ppm (t,3H), 2.33 ppm (s,3H), 2.51 ppm (d,2H), 3.35 ppm (s,3H), 5.06 ppm (s,2H), 5.80 ppm (s,1H), 7.87 ppm (d,1H), 8.03 ppm (d,1H): mass spectrum (m/e): 382(16) M⁺ |
| 13 | Cyanomethyl | Oil; ¹H—NMR (d₆-DMSO, 400 MHz): 2.33 ppm (s,3H), 3.35 ppm (s,3H), 5.24 ppm (s,2H), 5.81 ppm (s,1H), 7.91 ppm (d,1H), 8.09 ppm (d,1H); mass spectrum (m/e): 351(21) M⁺ |
| 14 | Acetylmethyl | Oil; ¹H—NMR (d₆-DMSO, 400 MHz): 2.17 ppm (s,3H), 2.33 ppm (s,3H), 3.35 ppm (s,3H), 5.05 ppm (s,2H), 5.81 ppm (s,1H), 7.87 ppm (d,1H), 8.03 ppm (d,1H); mass spectrum (m/e): 368(36) M⁺ |
| 15 | 2-Norbornanylmethyl (mixture of endo/exo form) | Oil; ¹H—NMR (d₆-DMSO, 400 MHz): 0.70–1.90 ppm (m,8H), 2.06–2.28 ppm (m,3H), 2.33 ppm (s,3H), 3.35 ppm (s,3H), 4.00–4.37 ppm (m,2H), 5.80 ppm (s,1H), 7.83 ppm (d,1H), 7.92 ppm (dd,1H); mass spectrum (m/e): 420(3.8) M⁺ |
| 16 | 1-(Methoxycarbonyl)-ethyl | Oil; ¹H—NMR (CDCl₃, 60 MHz): 1.60 ppm (d,3H), 2.36 ppm (s,3H), 3.49 ppm (s,3H), |

TABLE 2-continued

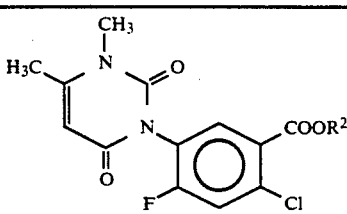

| Example | R² | Physical data |
|---|---|---|
| | | 3.81 ppm (s,3H), 5.36 ppm (q,1H), 5.77 ppm (s,1H), 7.39 ppm (d,1H), 8.00 ppm (d,1H); mass spectrum (m/e): 398(50) M⁺ |
| 17 | 1-(Ethoxycarbonyl)-ethyl (R-isomer) | Oil; $^1$H—NMR (CDCl$_3$, 400 MHz): 1.27 ppm (t,3H), 1.59 ppm (d,3H), 2.32 ppm (s,3H), 3.44 ppm (s,3H), 4.22 ppm (q,2H), 5.29 ppm (q,1H), 5.73 ppm (s,1H), 7.35 ppm (d,1H), 7.95 ppm (dd,1H); mass spectrum (m/e): 412(47) M⁺; $[\alpha]_{Dnm}^{20°\,C.} = -19.36°$ (CHCl$_3$, c = 1.07%) |
| 18 | 1-(Ethoxycarbonyl)-ethyl (S-isomer) | Oil; $^1$H—NMR (CDCl$_3$, 60 MHz): 1.29 ppm (t,3H), 1.64 ppm (d,3H), 2.36 ppm (s,3H), 3.50 ppm (s,3H), 4.29 ppm (q,2H), 5.48 ppm (q,1H), 5.81 ppm (s,1H), 7.44 ppm (d,1H), 8.04 ppm (d,1H); mass spectrum (m/e): 412(39) M⁺; $[\alpha]_{Dnm}^{20°\,C.} = +21.88°$ (CHCl$_3$, c = 0.99%) |
| 19 | n-Butoxycarbonyl-methyl | Oil; $^1$H—NMR (CDCl$_3$, 60 MHz): 0.9–1.68 ppm (m,7H), 2.77 ppm (s,3H), 3.45 ppm (s,3H), 4.26 ppm (t,2H), 4.88 ppm (s,2H), 5.77 ppm (s,1H), 7.45 ppm (d,1H), 8.10 ppm (d,1H); mass spectrum (m/e): 426(18) M⁺ |
| 20 | 1-[{2-[(α-Methyl)-ethylidene)imino-oxy]ethyl}oxy-carbonyl]-ethyl (R-isomer) | Oil; $^1$H—NMR (CDCl$_3$, 400 MHz): 1.59 ppm (dd,3H), 1.81 ppm (s,3H), 1.85 ppm (s,3H), 2.32 ppm (s,3H), 3.44 ppm (s,3H), 4.22 ppm (t,2H), 4.33–4.43 ppm (m,2H), 5.34 ppm (q,1H), 5.73 ppm (t,1H), 7.35 ppm (d,1H), 7.96 ppm (dd,1H); mass spectrum (m/e): 483(10) M⁺; $[\alpha]_{Dnm}^{20°\,C.} = -12.07°$ (CHCl$_3$, c = 1.07%) |

TABLE 2-continued

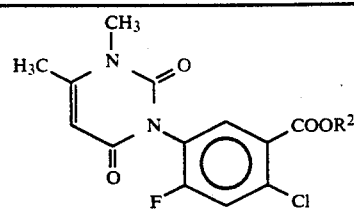

| Example | R² | Physical data |
|---|---|---|
| 21 | 1-(Isobutyloxy-carbonyl)-ethyl (R-isomer) | Oil; $^1$H—NMR (CDCl$_3$, 400 MHz): 0.92 ppm (d,6H), 1.60 ppm (d,3H), 1.95 ppm (q,1H), 2.32 ppm (s,3H), 3.43 ppm (s,3H), 3.90–3.99 ppm (m,2H), 5.32 ppm (q,1H), 5.73 ppm (s,1H), 7.36 ppm (d,1H), 7.96 ppm (q,1H); mass spectrum (m/e): 440(12) M⁺; $[\alpha]_{Dnm}^{20°\,C.} = -14.57°$ (CHCl$_3$, c = 1.07%) |
| 22 | 1-(tert.Butoxy-carbonyl)-ethyl | Oil; $^1$H—NMR (CDCl$_3$, 400 MHz): 1.46 ppm (s,9H), 1.54 ppm (d,3H), 1.56 ppm (s,2H), 2.32 ppm (s,3H), 3.44 ppm (s,3H), 5.17 ppm (q,1H), 5.73 ppm (s,1H), 7.35 ppm (d,1H), 7.93 ppm (q,1H); mass spectrum (m/e): 400(5) M⁺ |
| 23 | 1-(Propargyloxy-carbonyl)-ethyl (R-isomer) | Oil; $^1$H—NMR (CDCl$_3$, 400 MHz): 1.62 ppm (d,3H), 2.32 ppm (s,3H), 2.49 ppm (t,1H), 3.45 ppm (s,3H), 4.76 ppm (q,2H), 5.35 ppm (q,1H), 5.74 ppm (s,1H), 2.35 ppm (d,1H), 7.96 ppm (q,1H); mass spectrum (m/e): 422(22) M⁺; $[\alpha]_{Dnm}^{20°\,C.} = -16.05°$ (CHCl$_3$, c = 1.07%) |
| 24 | 1-(Ethoxycarbonyl)-1-methylethyl | Oil; $^1$H—NMR (CDCl$_3$, 400 MHz): 1.25 ppm (t,3H), 1.66 ppm (d,6H), 2.32 ppm (s,3H), 3.45 ppm (s,3H), 4.20 ppm (q,2H), 5.74 ppm (s,1H), 7.35 ppm (d,1H), 7.87 ppm (q,1H); mass spectrum (m/e): 426(9) M⁺ |
| 25 | Trimethylsilylmethyl | Resin $^1$H—NMR (CDCl$_3$, 400 MHz): 0.13 ppm (s,9H), 2.33 ppm (s,3H), 3.45 ppm (s,3H), 4.01 ppm (s,2H), 5.74 ppm (s,1H), 7.33 ppm (d,1H), 7.82 ppm (d,1H), |

TABLE 2-continued

[Structure: 1-methyl-6-methyl-uracil substituted on N with phenyl bearing COOR² (para to N), F, and Cl groups]

| Example | R² | Physical data |
|---|---|---|
| 26 | 2-(Trimethylsilyl)-ethyl | Resin; $^1$H—NMR (CDCl$_3$, 400 MHz): 0.06 ppm (s,9H), 1.08–1.15 ppm (m,2H), 2.31 ppm (s,3H), 3.44 ppm (s,3H), 4.35–4.41 ppm (m,2H), 5.73 ppm (s,1H), 7.33 ppm (d,1H), 7.87 ppm (d,1H), |
| 27 | Diethylphosphono-methyl | Resin; $^1$H—NMR (CDCl$_3$, 400 MHz): 1.34 ppm (t,6H), 2.33 ppm (s,3H), 3.44 ppm (s,3H), 4.19 ppm (m,4H), 4.59 ppm (d,2H), 5.73 ppm (s,1H), 7.37 ppm (d,1H), 7.93 ppm (d,1H). |
| 28 | 2-(Diethylphosphono)-ethyl | Resin; $^1$H—NMR (CDCl$_3$, 400 MHz): 1.32 ppm (t,6H), 2.23–2.33 ppm (m,2H), 2.33 ppm (s,3H), 3.44 ppm (s,3H), 4.06–4.18 ppm (m,4H), 4.50–4.58 ppm (m,2H), 5.73 ppm (s,1H), 7.36 ppm (d,1H), 7.91 ppm (d,1H) |
| 29 | 5-Norbornen-2-yl (mixture of endo/exo form) | M.p. 153–154° C. |
| 30 | 2-Cyanoethyl | Oil; $^1$H—NMR (d$_6$-DMSO, 200 MHz): 2.36 ppm (s,3H), 3.05 ppm (t,2H), 3.36 ppm (s,3H), 4.49 ppm (t,2H), 5.83 ppm (s,1H), 7.88 ppm (d,1H), 7.98 ppm (d,1H); mass spectrum (m/e): 365 (18), M$^+$ |
| 31 | 2-(Methylsulphonyl)-ethyl | M.p. 150–152° C. |
| 32 | 2-Norbornanyl (exo form) | Oil; $^1$H—NMR (CDCl$_3$, 200 MHz): 1.04–1.27 ppm (m,3H), 1.36–1.66 ppm (m,5H), 1.73–1.88 ppm (m,1H), 2.32 ppm (s,3H), 2.40–2.48 ppm (m,1H), 3.45 ppm (s,3H), 4.78–4.87 ppm (m,1H), 5.74 ppm (s,1H), 7.33 ppm (d,1H), 7.80 ppm (d,1H); mass spectrum (m/e): 406 (8.5), M$^+$ |
| 33 | 2-Phenoxyethyl | Oil; $^1$H—NMR (CDCl$_3$, 200 MHz): 2.31 ppm (s,3H), 3.43 ppm (s,3H), 4.24–4.32 ppm (m,2H), 4.60–4.68 ppm (m,2H), 5.73 ppm (s,1H), 6.88–7.00 ppm (m,3H), 7.23–7.40 ppm (m,3H), 7.87 ppm (d,1H); mass spectrum (m/e): 432 (5.6), M$^+$ |
| 34 | 2-Allyloxyethyl | Oil; $^1$H—NMR (d$_6$-DMSO, 200 MHz): 2.36 ppm (s,3H), 3.36 ppm (s,3H), 3.67–3.75 ppm (m,2H), 3.96–4.03 ppm (m,2H), 4.38–4.47 ppm (m,2H), 5.08–5.31 ppm (m,2H), 5.76–5.97 ppm (m,2H), 7.85 ppm (d,1H), 7.94 ppm (d,1H); infrared (CHCl$_3$): 1715 cm$^{-1}$ ($\nu$C=O), 1670 cm$^{-1}$ ($\nu$C—O) |
| 35 | 2-(Methoxycarbonyl)-1-methylethyl | Oil; $^1$H—NMR (CDCl$_3$, 200 MHz): 1.68 ppm (s,6H), 2.33 ppm (s,3H), 3.45 ppm (s,3H), 3.76 ppm (s,3H), 5.75 ppm (s,1H), 7.36 ppm (d,1H), 7.88 ppm (d,1H); mass spectrum (m/e): 412 (10) M$^+$ |
| 36 | 2-(tert.Butoxycarbonyl)-1-methylethyl | Oil; $^1$H—NMR (CDCl$_3$, 200 MHz): 1.45 ppm (s,9H), 1.64 ppm (s,6H), 2.33 ppm (s,3H), 3.45 ppm (s,3H), 5.54 ppm (s,1H), 7.65 ppm (d,1H), 7.80 ppm (d,1H); mass spectrum (m/e): 454 (2), M$^+$ |
| 37 | 1-Cyanoethyl | Oil; $^1$H—NMR (d$_6$-DMSO, 200 MHz): 1.69 ppm (d,3H), 2.33 ppm (s,3H), 3.36 ppm (s,3H), 5.75 ppm (q,1H), 5.82 ppm (s,1H), 7.92 ppm (d,1H), 8.92 ppm (d,1H); mass spectrum (m/e): 365 (28), M$^+$ |
| 38 | 1-(Ethoxycarbonyl)-1-methylpropyl | Oil; $^1$H—NMR (CDCl$_3$, 200 MHz): 0.98 ppm (t,3H), 1.26 ppm (t,3H), 1.68 ppm (d,3H), 1.64–2.36 ppm (m,2H), 2.33 ppm (d,3H), 3.46 ppm (s,3H), 4.08–4.26 ppm (m,2H), 5.75 ppm (d,1H), |

TABLE 2-continued

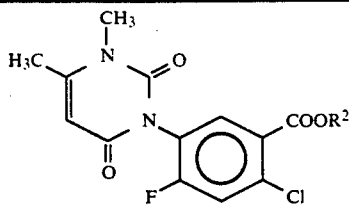

| Example | R² | Physical data |
|---|---|---|
| 39 | Methoxycarbonylmethyl | 7.35 ppm (d,1H), 7.84 ppm (d,1H); mass spectrum (m/e): 440 (4), M⁺ Oil; ¹H—NMR (CDCl₃, 200 MHz): 2.33 ppm (s,3H), 3.45 ppm (s,3H), 3.79 ppm (s,3H), 4.84 ppm (d,2H), 5.74 ppm (s,1H), 7.38 ppm (d,1H). 8.00 ppm (d,1H); mass spectrum (m/e): 384 (30), M⁺ |
| 40 | 1-(Isopropoxycarbonyl)-ethyl (R)-isomer | Oil; ¹H—NMR (CDCl₃, 400 MHz): 1.23–1.27 ppm (m,6H), 1.56–1.61 ppm (m,3H), 2.32 ppm (s,3H), 3.45 ppm (d,3H), 5.03–5.10 ppm (m,1H), 5.24 ppm (q,1H), 5.73 ppm (s,1H), 7.35 ppm (d,1H), 7.94 ppm (q,1H); $[\alpha]_D^{20} = -19.06°$ (CHCl₃, c = 0.61%) |

EXAMPLES 41–58

The compounds of formula I listed in Table 3 hereinafter are obtained analogously to the procedure described in Example 1 from 2-chloro-5-[3,6-dihydro-2,6-dioxo-3-methyl-4-trifluoromethyl-1(2H)-pyrimidinyl]-benzoic acid via its acid chloride:

TABLE 3

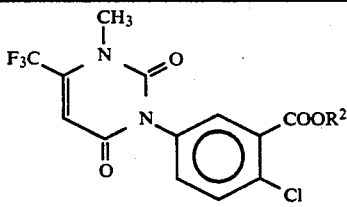

| Example | R² | Physical date |
|---|---|---|
| 41 | 2-Allyloxyethyl | Oil; ¹H-NMR (d₆-DMSO, 200 MHz): 3.41 ppm (s, 3H), 3.64–3.76 ppm (m, 2H), 3.96–4.03 ppm (m, 2H), 4.40–4.48 ppm (m, 2H), 5.09–5.32 ppm (m, 2H), 5.77–5.97 ppm (m, 1H), 6.56 ppm (s, 1H), 7.54 ppm (dd, 1H), 7.75 ppm (d, 1H), 7.80 ppm (d, 1H); Infrared (CHCl₃): 1730 cm⁻¹ (υC = 0), 1690 cm⁻¹ (υC = 0) |

TABLE 3-continued

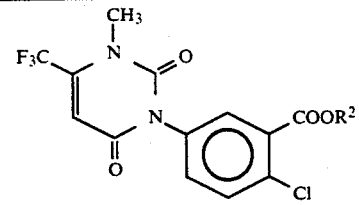

| Example | R² | Physical date |
|---|---|---|
| 42 | 2-Norbornanyl (exo form) | M.p. 126–127° C. |
| 43 | 2-(Methoxycarbonyl)-1-methylethyl | M.p. 156–157° C. |
| 44 | 1-(Isopropoxycarbonyl)-ethyl (S-isomers) | ¹H-NMR (d₆-DMSO, 200 MHz): 1.20 ppm (d, 3H), 1.23 ppm (d, 3H), 1.52 ppm (d, 3H), 3.40 ppm (s, 3H), 4.96 ppm (septet, 1H), 5.22 ppm (q, 1H), 6.57 ppm (s, 1H), 7.57 ppm (dd, 1H), 7.78 ppm (d, 1H), 7.86 ppm (d, 1H); mass spectrum (m/e): 462 (10), M⁺; $[\alpha]_D^{20} = +14.4°$ (CHCl₃, c = 0.6%) |
| 45 | 1-(Ethoxycarbonyl)-1-methylpropyl (racemate) | M.p. 135–137° C. |
| 46 | 1-(tert.Butoxycarbonyl)-1-methylethyl | M.p. 173–174° C. |
| 47 | 1-(Allyloxycarbonyl)-1-methylethyl | M.p. 109–111° C. |
| 48 | 1-(Cyclopentyloxycarbonyl)-1-methylethyl | M.p. 130–133° C. |
| 49 | 1-Carboxy-1-methylethyl | M.p. 201–203° C. |
| 50 | 2-Propargyloxyethyl | Oil; ¹H-NMR (d₆-DMSO, 200 MHz): 3.40 ppm (s, 3H), 3.44 ppm (t, 1H), 3.72–3.80 ppm (m, 2H), 4.19 ppm (d, 2H), 4.41–4.48 ppm (m, 2H), 6.55 ppm (s, 1H), 7.53 ppm (dd, 1H), 7.75 ppm (d, 1H), 7.78 ppm (d, 1H); mass spectrum (m/e): 430 (3), M⁺ |
| 51 | 1-Methyl-2-phenoxy-ethyl (racemate) | Oil; ¹H-NMR (d₆-DMSO, 200 MHz): 1.42 ppm (d, 3H), 3.40 ppm (s, 3H), 4.10–4.26 ppm (m, 2H), 5.36–5.50 ppm (m, 1H), 6.56 ppm (s, 1H), 6.86–7.01 ppm (m, 3H), 7.19–7.32 ppm (m, 2H), 7.51 ppm (dd, 1H), 7.69 ppm (d, 1H), 7.74 ppm (d, 1H); mass spectrum (m/e): 482 (5), M⁺ |
| 52 | 1-(Ethoxycarbonyl)-ethyl (S-isomer) | ¹H-NMR (d₆-DMSO, 200 MHz): 1.21 ppm (t, 3H), 1.53 ppm (d, 3H), 3.40 ppm (s, 3H), 4.17 ppm (q, 2H), 5.28 ppm (q, 1H), 6.35 ppm (s, 1H), 7.56 ppm (q, 1H), 7.77 ppm (d, 1H), 7.88 ppm (d, 1H), $[\alpha]_D^{20} = +12.4°$ |

TABLE 3-continued

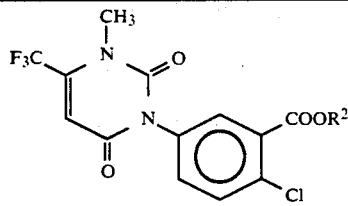

| Example | R² | Physical date |
|---|---|---|
| 53 | 1-(Ethoxycarbonyl)-1-methylethyl | (CHCl₃, c = 1.04%) ¹H-NMR (d₆-DMSO, 200 MHz): 1.19 ppm (t, 3H), 1.62 ppm (s, 6H), 3.40 ppm (s, 1H), 4.16 ppm (q, 2H), 6.55 ppm (s, 1H), 7.54 ppm (d, 1H), 7.76 ppm (d, 1H), 7.80 ppm (d, 1H); mass spectrum (m/e): 462 (4), M⁺ |
| 54 | (2-Methylpropionyl)methyl | M.p. 127–129° C. |
| 55 | 1-Acetylethyl | ¹H-NMR (CDCl₃, 200 MHz): 1.53 ppm (d, 3H), 2.25 ppm (s, 3H), 3.56 ppm (q, 3H), 5.33 ppm (q, 1H), 6.38 ppm (s, 1H), 7.33 ppm (q, 1H), 7.62 ppm (d, 1H), 7.84 ppm (d, 1H), |
| 56 | 1-Acetyl-1-methylethyl | M.p. 195–198° C. |
| 57 | 2-Ethoxycarbonyl-1-methylethyl | ¹H-NMR (CDCl₃, 200 MHz): 1.23 ppm (t, 3H), 1.42 ppm (d, 3H), 2.60 ppm (q, 1H), 2.80 ppm (q, 1H), 3.55 ppm (q, 3H), 4.14 ppm (q, 2H), 5.55 ppm (m, 1H), 6.38 ppm (s, 1H), 7.29 ppm (q, 1H), 7.59 ppm (d, 1H), 7.71 ppm (d, 1H), |
| 58 | 1-Cyano-1-methylethyl | M.p. 182–184° C. |

EXAMPLES 59–62

The compounds of formula I listed in Table 4 hereinafter are obtained analogously to the procedure described in Example 1 via its acid chloride:

TABLE 4

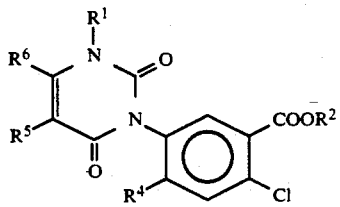

| Example | R¹ | R² | R⁴ | R⁵ | R⁶ | Physical data |
|---|---|---|---|---|---|---|
| 59 | CH₃ | 2-Allyloxyethyl | F | H | C₂F₅ | ¹H-NMR (CDCl₃, 200 MHz): 3.56–3.60 ppm (m, 3H), 3.72–3.80 ppm (m, 2H), 4.01–4.08 ppm (m, 2H), 4.44–4.52 ppm (m, 2H), 5.15–5.24 ppm (m, 1H), |

TABLE 4-continued

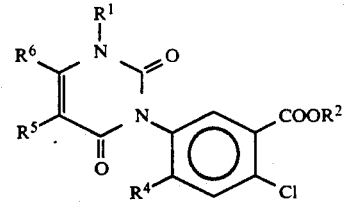

| Example | R¹ | R² | R⁴ | R⁵ | R⁶ | Physical data |
|---|---|---|---|---|---|---|
|  |  |  |  |  |  | 5.24–5.36 ppm (m, 1H), 5.80–6.01 ppm (m, 1H), 6.36 ppm (s, 1H), 7.40 ppm (d, 1H), 7.93 ppm (d, 1H); infrared (CHCl₃): 1735 cm⁻¹ (νC = O), 1680 cm⁻¹ (νC = O) |
| 60 | CHF₂ | 2-Allyloxyethyl | F | H | CH₃ | ¹H-NMR (d₆-DMSO, 200 MHz): 2.43 ppm (s, 3H), 3.66–3.74 ppm (m, 2H), 3.97–4.03 ppm (m, 2H), 4.40–4.47 ppm (m, 2H), 5.09–5.18 ppm (m, 1H), 5.18–5.31 ppm (m, 1H), 5.78–5.97 ppm (m, 1H), 6.08 ppm (s, 1H), 7.90 ppm (d, 1H), 7.90 ppm (t, 1H), 8.11 ppm (d, 1H); infrared (CHCl₃): 1735 cm⁻¹ (νC = O), 1695 cm⁻¹ (νC = O) |
| 61 | CHF₂ | 1-(Ethoxycarbonyl)-1-methylethyl | H | H | CH₃ | M.p. 91–93° C. |
| 62 | CH₃ | 2-Allyloxyethyl | F | F | CF₃ | ¹H-NMR (d₆-DMSO, 200 MHz): 3.40–3.44 ppm (m, 3H), 3.67–3.74 ppm (m, 2H), 3.96–4.03 ppm (m, 2H), 4.41–4.48 ppm (m, 2H), 5.10–5.18 ppm (m, 1H), 5.18–5.32 ppm (m, 1H), 5.78–7.98 ppm (m, 1H), 7.95 ppm (d, 1H), 8.06 ppm (d, 1H); infrared (CHCl₃): 1760 cm⁻¹ (νC = O), 1690 cm⁻¹ (νC = O) |

EXAMPLE 63

2-Allyloxyethyl 2-chloro-4-fluoro-5-[2-methoxy-6-oxo-4-trifluoromethyl-1(6H)-pyrimidinyl]-benzoate, m.p. 74°–77° C. is obtained analogously to the procedure described in Example 1 from 2-chloro-4-fluoro-5-[2-methoxy-6-oxo-4-trifluoromethyl-1(6H)-pyrimidinyl]-benzoic acid via its acid chloride and 2-allyloxyethanol.

EXAMPLE 64

A mixture of 1.5 g of 1-methoxycarbonyl-1-methylethyl 2-chloro-5-[3,6-dihydro-3 4-dimethyl-2,6-dioxo-1(2H)-pyrimidinyl]-4-fluorobenzoate and 0.4 g of copper(I) cyanide in 20 ml of 1,3-dimethyl-3,4,5,6-tetrahydro-2(1H)-pyrimidinone is heated to 220° C. under nitrogen for 6 hours. After cooling to room temperature the mixture is filtered and the filtrate is dissolved in 200 ml of ethyl acetate. The solution is washed four times with 50 ml of water each time, the combined organic phases are dried and concentrated under reduced pressure. In this manner there is obtained 1-methoxycarbonyl-1-methylethyl 2-cyano-5-[3,6-dihydro-3,4-dimethyl-2,6-dioxo-1(2H)-pyrimidinyl]-4-fluorobenzoate, mass spectrum (m/e); 403 10) M+.

EXAMPLE 65

1-Cyanoethyl 2-cyano-5-[3,6-dihydro-3,4-dimethyl-2,6-dioxo-1(2H)-pyrimidinyl]-4-fluorobenzoate, mass spectrum (m/e): 356 (17) M+, is obtained analogously to the procedure described in Example 64 from 1-cyanoethyl 2-chloro-5-[3,6-dihydro-3,4-dimethyl-2,6-dioxo-1(2H)-pyrimidinyl]-4-fluorobenzoate and copper I) cyanide.

EXAMPLE 66

4.9 g of sodium hydride (50% dispersion in white oil) are added to 120 ml of dimethylformamide while stirring and the mixture is cooled to −5° C. At this temperature a solution of 22.4 g of ethyl 3-amino-4,4,4-trifluorocrotonate in 180 ml of diethyl ether is added dropwise during 30 minutes. The reaction mixture is stirred at room temperature for one hour and thereafter cooled to −65° C. A solution of 28 g of ethyl 2-(2-chloro-5-isocyanato-benzoyloxy)-2-methylpropionate in 100 ml of dimethylformamide is now added dropwise during 30 minutes. The reaction mixture is stirred at −65° C. for 2 hours; thereafter it is left to warm to room temperature. The reaction mixture is introduced into 300 ml of 1N hydrochloric acid at 0° C. The mixture is extracted twice with 300 ml of ethyl acetate each time. The organic phases are back-washed once with 200 ml of water and once with 200 ml of saturated sodium chloride solution, dried over anhydrous sodium sulphate and concentrated under reduced pressure. The residue is recrystallized from ethyl acetate/n-hexane. There is obtained ethyl 2-{2-chloro-5-[3,6-dihydro-2,6-dioxo-4-trifluoromethyl-1(2H)-pyrimidinyl]-benzoyloxy}-2-methylpropionate, m.p. 176°–177° C.

EXAMPLE 67

Ethyl 2-{2-chloro-5-[3,6-dihydro-2,6-dioxo-4-pentafluoroethyl-1(2H)-pyrimidinyl]-benzoyloxy}-2-methyl-propionate, m.p. 141°–143° C., is obtained analogously to the procedure described in Example 66 from ethyl 3-amino-4,4,5,5,5-pentafluoropent-2-enoate and ethyl 2-(2-chloro-5-isocyanato-benzoyloxy)-2-methyl-propionate.

EXAMPLE 68

2.5 g of ethyl 2-{2-chloro-5-[3,6-dihydro-2,6-dioxo-4-pentafluoroethyl-1(2H)-pyrimidinyl]-benzoyloxy}-2-methyl-propionate and 0.7 g of potassium carbonate are dissolved in 25 ml of water and 15 ml of dioxan. 0.65 g of dimethyl sulphate is added thereto and the reaction mixture is stirred at room temperature for 38 hours. Thereafter, 100 ml of water are added thereto; and the mixture is extracted twice with 200 ml of ethyl acetate each time. The organic phases are back-washed once with 150 ml of saturated sodium chloride solution, dried over anhydrous sodium sulphate and concentrated under reduced pressure. The residue is purified by chromatography on silica gel with ethyl acetate/n-hexane (1:4). There is thus obtained ethyl 2-{2-chloro-5-[3,6-dihydro-2,6-dioxo-3-methyl 4-pentafluoroethyl-1(2H)-pyrimidinyl]-benzoyloxy}-2-methyl-propionate which is recrystallized from diethyl ether/n-hexane; m.p. 114°–115° C.

EXAMPLE 69

Analogously to the procedure described in Example 68, from ethyl 2-{2-chloro-5-[3,6-dihydro-2,6-dioxo-4-trifluoromethyl-1(2H)-pyrimidinyl]-benzoyloxy}-2-methyl-propionate and diethyl sulphate there is obtained ethyl 2-{2-chloro-5-{3,6-dihydro-2,6-dioxo-3-ethyl-4-trifluoromethyl-1(2H)-pyrimidinyl]-benzoyloxy}-2-methylpropionate as an oil;

$^1$H-NMR (d$_6$-DMSO, 200 MHz): 1.20 ppm (t, 3H). 1.24 ppm (t, 3H), 1.62 ppm (s, 6H). 3.87 ppm (q. 2H). 4.16 ppm (q, 2H), 6.55 ppm (s, 1H), 7.57 ppm (dd, 1H), 7.75 ppm (d, 1H), 7.82 ppm (d, 1H).

EXAMPLE 70

0.35 g of sodium hydride (50% dispersion in white oil) is added to 40 ml of dimethylformamide while stirring. 2.9 g of ethyl 2-{2-chloro-5-[3,6-dihydro-2,6-dioxo-4-trifluoromethyl-1(2H)-pyrimidinyl]-benzoyloxy}-2-methyl-propionate [sic] are added portionwise as the solid. After completion of the addition the mixture is stirred at room temperature for a further hour. 1.2 g of allyl bromide are now added in one portion. The reaction mixture is stirred at room temperature for 18 hours and thereafter introduced into 100 ml of water at 0° C. The mixture is extracted twice with 150 ml of ethyl acetate each time. The organic phases are washed once with 100 ml of saturated sodium chloride solution, dried over anhydrous sodium sulphate and concentrated under reduced pressure. The residue is purified by chromatography over silica gel with ethyl acetate/n-hexane (1:4). There is obtained ethyl 2-{2-chloro-5-[3,6-dihydro-2,6-dioxo-3-(2-propenyl)-4-trifluoromethyl-1(2H)-pyrimidinyl]-benzoyloxy}-2-methyl-propionate as an oil;

$^1$H-NMR (d$_6$-DMSO, 200 MHz): 1.19 ppm (t, 3H). 1.62 ppm (s, 6H), 4.15 ppm (q, 2H), 4.42–4.53 ppm (m, 2H), 5.14–5.34 ppm (m, 2H), 5.78–6.00 ppm (m, 1H). 6.60 ppm (s, 1H), 7.58 ppm (dd, 1H), 7.75 ppm (d, 1H), 7.83 ppm (d, 1H).

EXAMPLE 71

Analogously to the procedure described in Example 70, from ethyl 2-{2-chloro-5-[3 6-dihydro-2.6-dioxo-4-trifluoromethyl-1(2H)-pyrimidinyl]-benzoyloxy}-2-methyl-propionate and propargyl bromide there is obtained ethyl 2-{2-chloro-5-[3,6-dihydro-2,6-dioxo-3-(3-propynyl)-4-trifluoromethyl-1(2H)-pyrimidinyl]-benzoyloxy}-2-methyl-propionate as an oil;

$^1$H-NMR (d$_6$-DMSO, 200 MHz): 1.19 ppm (t, 3H). 1.62 ppm s, 6H), 3.43 ppm (t, 1H). 4.16 ppm (q, 2H). 4.63 ppm (d, 2H), 6.64 ppm (s. 1H), 7.60 ppm (dd, 1H), 7.76 ppm (d, 1H), 7.85 ppm (d, 1H).

EXAMPLE 72

A mixture of 9 g of ethyl 2-[2-chloro-4-fluoro-5-(3-oxo-pentanoyl)-aminobenzoyloxy]-2-methyl-propionate, 2.7 g of urethane and 0.9 g of p-toluenesulphonic acid in 150 ml of benzene is heated. During the reaction period of five hours the water which is formed in the reaction is separated. The solvent is then evaporated under reduced pressure. There is thus obtained crude ethyl 2-{2-chloro-4-fluoro-5-[3-(ethoxycarbonyl)amino-pent-2-enoyl]amino-benzoyloxy}-2-methyl-propionate.

0.6 g of sodium is dissolved completely in 50 ml of ethyl α-hydroxyisobutyrate. This solution is combined with the crude ethyl 2-{2-chloro-4-fluoro-5-[3-(ethoxycarbonyl)amino-pent-3-enoyl]amino-benzoyloxy}-2-methylpropionate and stirred at 120° C. for 4 hours. After cooling, this reaction mixture is introduced into 100 ml of 1N hydrochloric acid at 0° C. The mixture is extracted twice with 150 ml of ethyl acetate each time, back-washed twice with 200 ml of water each time, dried over anhydrous magnesium sulphate and concentrated under reduced pressure. The residue is purified by chromatography on silica gel with ethyl acetate/n-hexane (3:2). There is obtained ethyl 2-{2-chloro-4-fluoro-5-[3,6-dihydro-2,6-dioxo-4-ethyl-1(2H)-pyrimidinyl]-benzoyloxy}-2-methylpropionate which is recrystallized from diethyl ether/n-hexane; m.p. 166°–167° C.

EXAMPLE 73

A mixture of 1.2 g of ethyl 2-{2-chloro-4-fluoro-5-[3,6-dihydro-2,6-dioxo-4-ethyl-1(2H)-pyrimidinyl]-benzoyloxy}-2-methyl-propionate, 0.4 g of dimethyl sulphate and 0.7 g of potassium bicarbonate in 30 ml of acetone is heated to reflux temperature for 3 hours. The reaction mixture is treated with 200 ml of water and extracted twice with 150 ml of ethyl acetate each time. The organic phases are washed once with 100 ml of saturated sodium chloride solution, dried over anhydrous sodium sulphate and concentrated under reduced pressure. The residue is purified by chromatography over silica gel with ethyl acetate/n-hexane (3:2). There is thus obtained ethyl 2-{2-chloro-4-fluoro-5- 3,6-dihydro-2,6-dioxo-3-methyl-4-ethyl-1(2H)-pyrimidinyl]-benzoyloxy}-2-methylpropionate as an oil, $^1$H-NMR ($d_6$-DMSO): 1.19 ppm (t, 6H), 1.61 ppm (s, 6H), 2.66 ppm (q, 2H), 3.37 ppm (s, 3H), 4.15 ppm (q. 2H). 5.72 ppm (s, 1H), 7 86 ppm (d, 1H), 7.99 ppm (d, 1H).

II. Preparation of the starting materials of formulae XII, XV and XVIII

EXAMPLE 74

10 g of 2-chloro-4-fluoro-5-nitro-benzoic acid, 5 ml of thionyl chloride and 2 drops of N,N-dimethylformamide are heated to reflux temperature for 4 hours. Subsequently, the reaction mixture is evaporated to dryness and dissolved in 20 ml of dioxan. This solution, which consists mainly of the acid chloride of the above-mentioned benzoic acid and the solvent is added dropwise to a solution of 9.1 g of ethyl -hydroxy-isobutyrate, 7 ml of triethylamine and 100 mg of 4-(dimethylamino)pyridine in 35 ml of dioxan. The reaction mixture is then heated to reflux temperature for 24 hours. Then, the reaction mixture is left to cool and is treated with 200 ml of 2N hydrochloric acid. The mixture is now extracted three times with 250 ml of ethyl acetate each time. The organic phases are washed once with 200 ml of 2N hydrochloric acid, once with 200 ml of water, once with 200 ml of 2N potassium bicarbonate solution and twice with 200 ml of saturated sodium chloride solution each time, dried over anhydrous magnesium sulphate and evaporated under reduced pressure. The residue is purified by chromatography over silica gel with ethyl acetate/n-hexane (1:4). In this manner there is obtained ethyl 2-(2-chloro-4-fluoro-5-nitro-benzoyloxy)-2-methyl propionate which is recrystallized from diisopropyl ether/n-hexane; m.p. 55°–57° C.

A mixture of 10 g of finely powdered iron. 50 ml of ethanol, 11 ml of water and 1 ml of concentrated hydrochloric acid is heated to 65° C. while stirring. To this mixture is added dropwise during 2 hours a solution of 15 g of ethyl 2-(2-chloro-4-fluoro-5-nitro-benzoyloxy)-2-methyl-propionate in 15 ml of ethanol in such a manner that the temperature does not rise above 80° C. After completion of the addition the reaction mixture is stirred at 70° C. for a further 16 hours. After cooling the reaction mixture is suction filtered over Celite ®. The Celite ® is rinsed well with water and with ethyl acetate. The filtrate is adjusted to pH 8 with 2N potassium bicarbonate solution. It is once more filtered over Celite ® and again rinsed with water and ethyl acetate. The filtrate is now extracted three times with 400 ml of ethyl acetate each time. The organic phases are back-washed twice with 300 ml of saturated sodium chloride solution each time, dried over anhydrous magnesium sulphate and evaporated under reduced pressure. The residue is fractionated in a high vacuum and distilled. In this manner there is obtained ethyl 2-(5-amino-2-chloro-4-fluoro-benzoyloxy)-2-methylpropionate, b.p. 146°–151° C./0.07 torr.

EXAMPLE 75

Analogously to the procedure described in Example 74, from 2-chloro-5-nitro-benzoic acid via its acid chloride and ethyl α-hydroxy-isobutyrate there is obtained ethyl 2-(2-chloro-5-nitro-benzoyloxy)-2-methyl-propionate, m.p. 64°–66° C., which is subsequently reduced to ethyl 2-(5-amino-2-chloro-benzoyloxy)-2-methyl-propionate. B.p. 200°–230° C./0.1 torr;

$^1$H-NMR (CDCl$_3$, 200 MHz : 1.28 ppm (t, 3H), 1.69 ppm (s, 6H), 3.79 ppm (s, 2H), 4.23 ppm (q, 2H), 6.72 ppm (dd, 1H), 7.10 ppm (d, 1H), 7.19 ppm (d, 1H).

EXAMPLE 76

A solution of 40 g of diphosgene in 150 ml of ethyl acetate is heated to 65° C. while stirring. To this solution is added dropwise a solution of 40 g of ethyl 2-(5-amino-2-chloro-benzoyloxy)-2-methyl-propionate in 70 ml of ethyl acetate. After completion of the addition the reaction mixture is heated to reflux temperature for 3 hours. Thereafter, the solvent is distilled off. The residue is distilled in a bulb-tube at 200°–230° C. and 0.1 torr. In this manner there is obtained ethyl 2-(2-chloro-5-isocyanato-benzoyloxy)-2-methyl-propionate, $^1$H-NMR (CDCl$_3$, 200 MHz): 1.29 ppm (t, 3H), 1.71 ppm (s, 6H), 4.25 ppm (q, 2H), 7.14 ppm (dd, 1H 7.40 ppm (d, 1H), 7.52 ppm (d, 1H).

EXAMPLE 77

5.7 g of 2,2-dimethyl-1,3-dioxane-4,6-dione "Meldrum's acid") and 6.3 ml of pyridine are placed in 25 ml of methylene chloride and the mixture is cooled to 0° C. while stirring. At this temperature 3.8 ml of propionyl chloride are added dropwise during 30 minutes. The reaction mixture is then stirred at room temperature for one hour and thereafter introduced at 0° C. into 100 ml of 1N hydrochloric acid. The mixture is extracted rapidly twice with 250 ml of diethyl ether each time. The organic phases are washed twice with 150 ml of saturated sodium chloride solution each time, dried over anhydrous magnesium sulphate and concentrated. The residue is taken up in 50 ml of toluene. 12 g of ethyl 2-(5-amino-2-chloro-4-fluoro-benzoyloxy)-2-methyl-propionate are added thereto and the mixture is heated to reflux temperature for 4 hours. The reaction mixture is stirred for 16 hours, during which it cools to room temperature. The reaction mixture is introduced into 150 ml of 1N hydrochloric acid. The mixture is extracted three times with 250 ml of diethyl ether each time. The organic phases are back-washed twice with 150 ml of saturated sodium chloride solution each time, dried over anhydrous magnesium sulphate and concentrated under reduced pressure. The residue is purified by chromatography on silica gel with ethyl acetate/n-hexane (1:1). In this manner there is obtained ethyl 2-[2-chloro-4-fluoro-5-(3-oxo-pentanoyl)-amino-benzoyloxy]-2-methyl-propionate as an oil.

$^1$H-NMR (CDCl$_3$, 200 MHz): 1.14 ppm (t, 3H), 1.27 ppm (t, 3H), 1.70 ppm s, 6H). 2.63 ppm q, 2H). 3.63 ppm (s, 2H), 4.23 ppm (q, 2H), 7.24 ppm (d, 1H), 8.82 ppm (d, 1H), 9.70 ppm (s, 1H).

III. Formulation Examples:

EXAMPLE 78

An emulsifiable concentrate contains the following ingredients:

| Compound in accordance with the invention (active ingredient) | 50 g/l |
|---|---|
| N-Methylpyrrolidone (solubilizer) | 200 g/l |
| Nonylphenol-(10)ethoxylate (non-ionic emulsifer) | 50 g/l |
| Calcium dodecylbenzenesulphonate (anionic emulsifier) | 25 g/l |
| Mixture of alkylbenzenes (solvent) | ad 1000 ml |

The active ingredient and the emulsifiers are dissolved in the solubilizer while stirring and the solution is made up to 1 liter with the solvent.

The resulting emulsifiable concentrate can be emulsified in water and then gives a ready-for-use spray liquor having the desired concentration.

EXAMPLE 79

For the manufacture of a 25% spray powder the ingredients listed hereinafter are mixed with one another:

| Compound in accordance with the invention (active ingredient) | 25 g |
|---|---|
| Silicic acid, hydrated (carrier material, milling aid) | 5 g |
| Sodium lauryl sulphate (wetting agent) | 1 g |
| Sodium lignosulphonate (dispersing agent) | 2 g |
| Kaolin (carrier material) | 67 g |
| | 100 g |

Subsequently, the mixture is finely milled using a pinned disc mill or comparable milling aggregate.

Upon stirring into water the resulting spray powder gives a fine suspension which is suitable as a ready-for-use spray liquor.

We claim:

1. A compound of the formula

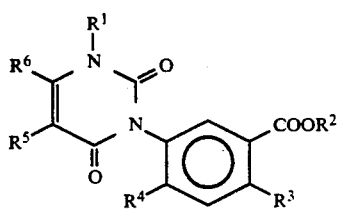

I wherein $R^1$ signifies hydrogen, $C_{1-4}$-alkyl, $C_3$ or 4-alkenyl, $C_3$ or 4-alkynyl or $C_{1-4}$-haloalkyl, $R^2$ signifies $C_{1-6}$-alkylsulphonyl-$C_{1-4}$-alkyl, di($C_{1-6}$-alkyl)phosphono-$C_{1-4}$-alkyl, tri($C_{1-6}$-alkyl)silyl-$C_{1-4}$-alkyl, $C_{2-7}$-alkanoyl-$C_{1-4}$-alkyl, carboxy-$C_{1-4}$-alkyl, {[$C_{3-9}$-(α-alkylalkylidene)]iminooxy-($C_{1-6}$-alkoxy)carbonyl}-$C_{1-4}$-alkyl, ($C_{3-6}$-alkenyloxy)-carbonyl-$C_{1-4}$-alkyl, ($C_{3-6}$-alkenyloxy-$C_{1-4}$-alkyl, $C_{3-8}$-cycloalkenyloxy-$C_{1-4}$-alkyl, $C_{5-8}$-cycloalkenyl, $C_{6-8}$-bicycloalkyl, $C_{6-8}$-bicycloalkenyl, $C_{2-7}$-cyanoalkyl or $C_{3-6}$-alkynyloxy-$C_{1-4}$-alkyl, $R^3$ signifies halogen or cyano, $R^4$ signifies hydrogen or halogen, $R^5$ signifies hydrogen, fluorine or $C_{1-4}$-alkyl and $R^6$ signifies $C_{1-4}$-alkyl or $C_{1-4}$-haloalkyl or $R^5$ and $R^6$ together form trimethylene or tetramethylene, or the corresponding enol ether of a compound of formula I in which $R^1$ is other than hydrogen or $C_{1-4}$-haloalkyl or a salt of a of formula I in which $R^1$ signifies hydrogen.

2. A compound according to claim 1, wherein $R^2$ is other than carboxy-$C_{1-4}$-alkyl, $R^5$ signifies hydrogen, fluorine or $C_{1-4}$-alkyl and $R^6$ signifies $C_{1-4}$-alkyl or $C_{1-4}$-haloalkyl or an enol ether or salt thereof.

3. A compound according to claim 1 or 2, wherein $R^1$ signifies methyl, $R^3$ signifies chlorine or bromine, $R^4$ signifies hydrogen or fluorine, $R^5$ signifies hydrogen, fluorine or methyl and $R^6$ signifies methyl, trifluoromethyl or pentafluoromethyl.

4. A compound according to claim 1, wherein $R^3$ signifies cyano.

5. A compound according to any one of claims 1, 2 or 4, wherein $R^2$ signifies $C_{2-7}$-alkanoyl-$C_{1-4}$-alkyl, ($C_{1-6}$-alkoxy)carbonyl-$C_{1-4}$-alkyl, {[$C_{3-9}$-(α-alkylalkylidene)-]iminooxy-($C_{1-6}$-alkoxy)carbonyl}-$C_{1-4}$-alkyl, ($C_{3-6}$-alkenyloxy)carbonyl-$C_{1-4}$-alkyl, ($C_{3-6}$-alkynyloxy)carbonyl-$C_{1-4}$-alkyl or ($C_{3-8}$-cycloalkyloxy)carbonyl-$C_{1-4}$-alkyl.

6. A compound according to claim 2, ethyl 2-{2-chloro-5-[3,6-dihydro-3,4-dimethyl-2,6-dioxo-1(2H)-pyrimidinyl]-4-fluorobenzoyloxy}-2-methyl-propionate.

7. A compound according to claim 1, selected from:
methyl 2-{2-chloro-5-[3,6-dihydro-3,4-dimethyl-2,6-dioxo-1(2H)-pyrimidinyl]-4-fluorobenzoyloxy]-2-methylpropionate,
tert.butyl 2-{2-chloro-5-[3,6-dihydro-3,4-dimethyl-2,6-dioxo-1(2H)-pyrimidinyl]-4-fluorobenzoyloxy}-2-methyl-propionate,
ethyl 2-ethyl-2-{2-chloro-5-[3,6-dihydro-3,4-dimethyl-2,6-dioxo-1(2H)-pyrimidinyl]-4-fluorobenzoyloxy}-propionate,
methyl 2-{2-chloro-5-[3,6-dihydro-2,6-dioxo-3-methyl-4-trifluoromethyl-1(2H)-pyrimidinyl]-benzoyloxy}-2-methyl-propionate,
isopropyl 2-{2-chloro-5-[3,6-dihydro-2,6-dioxo-3-methyl-4-trifluoromethyl-1(2H)-pyrimidinyl]-benzoyloxy}-propionate,
ethyl 2-ethyl-2-[2-chloro-5-[3,6-dihydro-2,6-dioxo-3-methyl-4-trifluoromethyl-1(2H)-pyrimidinyl]-benzoyloxy}-propionate,
tert.butyl 2-[2-chloro-5-[3,6-dihydro-2,6-dioxo-3-methyl-4-trifluoromethyl-1(2H)-pyrimidinyl]-benzoyloxy}-2-methyl-propionate,
allyl 2-{2-chloro-5-[3,6-dihydro-2,6-dioxo-3-methyl-4-trifluoromethyl-1(2H)-pyrimidinyl]-benzoyloxy}-2-methyl-propionate, cyclopentyl 2-{2-chloro-5-[3,6-dihydro-2,6-dioxo-3-methyl-4-trifluoromethyl-1(2H)-pyrimidinyl]-benzoyloxy}-2-methyl-propionate, ethyl 2-[2-chloro-5-[3,6-dihydro-2,6-dioxo-3-methyl-4-trifluoromethyl-1(2H)-pyrimidinyl]-benzoyloxy}-propionate, ethyl 2-[2-chloro-5-[3,6-dihydro-2,6-dioxo-3-methyl-4-trifluoromethyl-1(2H)-pyrimidinyl]-benzoyloxy}-2-methyl-propionate, 1-acetylethyl 2-chloro-5-[3,6-dihydro-2,6-dioxo-3-methyl-4-trifluoromethyl-1(2H)-pyrimidinyl]-benzoate and ethyl 3-{2-chloro-5-[3,6-dihydro-2,6-dioxo-3-methyl-4-trifluoromethyl-1(2H)-pyrimidinyl]-benzoyloxy}-butanoate.

8. A weed control composition, which comprises effective amount of at least one compound of the formula

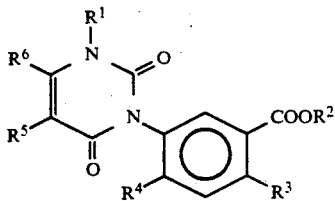

wherein
R$^1$ signifies hydrogen, C$_{1-4}$-alkyl, C$_{3\ or\ 4}$-alkenyl, C$_{3\ or\ 4}$-alkynyl or C$_{1-4}$-haloalkyl,
R$^2$ signifies C$_{1-6}$-alkylsulphonyl-C$_{1-4}$-alkyl, di(C$_{1-6}$-alkyl)phosphono-C$_{1-4}$-alkyl, tri(C$_{1-6}$-alkyl)silyl-C$_{1-4}$-alkyl, C$_{2-7}$-alkanoyl-C$_{1-4}$-alkyl, carboxy-C$_{1-4}$-alkyl, (C$_{1-6}$-alkoxy)carbonyl-C$_{1-4}$-alkyl, {[C$_{3-9}$-(α-alkylalkylidene)]iminooxy-(C$_{1-6}$-alkoxy)carbonyl}-C$_{1-4}$-alkyl, (C$_{3-6}$-alkenyloxy)carbonyl-C$_{1-4}$-alkyl, (C$_{3-6}$-alkynyloxy)carbonyl-C$_{1-4}$-alkyl, (C$_{3-8}$-cycloalkyloxy)carbonyl-C$_{1-4}$-alkyl, phenoxy-C$_{1-}$-alkyl, C$_{3-6}$-alkenyloxy-C$_{1-4}$-alkyl, C$_{3-8}$-cycloalkenyloxy-C$_{1-4}$-alkyl, C$_{5-8}$-cycloalkenyl, C$_{6-8}$-bicycloalkyl, C$_{6-8}$-bicycloalkenyl, C$_{2-7}$-cyanoalkyl or C$_{3-6}$-alkynyloxy-C$_{1-4}$-alkyl,
R$^3$ signifies halogen or cyano,
R$^4$ signifies hydrogen or halogen,
R$^5$ signifies hydrogen, fluorine or C$_{1-4}$-alkyl and
R$^6$ signifies C$_{1-4}$-alkyl or C$_{1-4}$-haloalkyl or
R$^5$ and R$^6$ together form trimethylene or tetramethylene, or of an enol ether of such a compound 1 in which R$^1$ is other than hydrogen or C$_{1-4}$-haloalkyl or of a salt of such a compound I in which R$^1$ signifies hydrogen, as well as formulation adjuvants.

9. A weed control composition according to claim 8, wherein R$^2$ in formula I is other than carboxy-C$_{1-4}$-alkyl, R$^5$ signifies hydrogen, fluorine or C$_{1-4}$-alkyl and R$^6$ signifies C$_{1-4}$-alkyl or C$_{1-4}$-haloalkyl, 10. A weed control composition according to claim 9, which comprises an effective amount of ethyl 2-{2-chloro-5-[3,6-dihydro-3,4-dimethyl-2,6-dioxo-1(2H)-pyrimidinyl]-4-fluorobenzoyloxy}-2-methyl-propionate as well as formulation adjuvants.

11. A weed control composition according to claim 8, which comprises an effective amount of at least one compound selected from the group
methyl 2-{2-chloro-5-[3,6-dihydro-3,4-dimethyl-2,6-dioxo-1(2H)-pyrimidinyl]-4-fluorobenzoyloxy}-2-methyl-propionate,
tert.butyl 2-{2-chloro-5-[3,6-dihydro-3,4-dimethyl-2,6-dioxo-1(2H)-pyrimidinyl]-4-fluorobenzoyloxy}-2-methyl-propionate,
ethyl 2-ethyl-2-{2-chloro-5-[3,6-dihydro-3,4-dimethyl-2,6-dioxo-1(2H)-pyrimidinyl]-4-fluorobenzoyloxy}-propionate,
methyl 2-{2-chloro-5-[3,6-dihydro-2,6-dioxo-3-methyl-4-trifluoromethyl-1(2H)-pyrimidinyl]-benzoyloxy}-2-methyl-propionate,
isopropyl 2-{2-chloro-5-[3,6-dihydro-2,6-dioxy-3-methyl-4-trifluoromethyl-1(2H)-pyrimidinyl]-benzoyloxy}-propionate,
ethyl 2-ethyl-2-{2-chloro-5-[3,6-dihydro-2,6-dioxo-3-methyl-4-trifluoromethyl-1(2H)-pyrimidinyl]-benzoyloxy}-propionate,
tert.butyl 2-{2-chloro-5-[3,6-dihydro-2,6-dioxo-3-methyl-4-trifluoromethyl-1(2H)-pyrimidinyl]-benzoyloxy}-2-methyl-propionate,
allyl 2-{2-chloro-5-[3,6-dihydro-2,6-dioxo-3-methyl-4-trifluoromethyl-1(2H)-pyrimidinyl]-benzoyloxy}-2-methyl-propionate,
cyclopentyl 2-{2-chloro-5-[3,6-dihydro-2,6-dioxo-3-methyl-4-trifluoromethyl-1(2H)-pyrimidinyl]-benzoyloxy}-2-methyl-propionate,
ethyl 2-[2-chloro-5-[3,6-dihydro-2,6-dioxo-3-methyl-4-trifluoromethyl-1(2H)-pyrimidinyl]-benzoyloxy}-propionate,
ethyl 2-[2-chloro-5-[3,6-dihydro-2,6-dioxo-3-methyl-4-trifluoromethyl-1(2H)-pyrimidinyl]-benzoyloxy}-2-methyl-propionate,
1-acetylethyl 2-chloro-5-[3,6-dihydro-2,6-dioxo-3-methyl-4-trifluoromethyl-1(2H)-pyrimidinyl]-benzoate and
ethyl 3-{2-chloro-5-[3,6-dihydro-2,6-dioxo-3-methyl-4-trifluoromethyl-1(2H)-pyrimidinyl]-benzoyloxy}-butanoate, as well as formulation adjuvants.

12. A method for the control of weeds, which process comprises treating the locus to be protected against weeds and/or the weeds with an effective amount of a compound, enol ether or salt in accordance with claim 1.

13. A method for the control of weeds, which method comprises treating the locus to be protected against weeds and/or the weeds with a effective amount of a compound, enol ether or salt in accordance with claim 2.

14. A method for the control of weeds, which process comprises treating the locus to be protected against weeds and/or the weeds with an effective amount of a composition in accordance with claim 8.

15. A method for the control of weeds, which method comprises treating the locus to be protected against weeds and/or the weeds with an effective amount of a composition in accordance with claim 9.

* * * * *